(12) United States Patent
Bosserhoff et al.

(10) Patent No.: US 10,828,281 B2
(45) Date of Patent: Nov. 10, 2020

(54) NON-HYDROPHOBIC COMPOUNDS FOR USE IN TREATING METASTASIS AND/OR CARTILAGE DEFECT

(71) Applicant: Friedrich-Alexander-Universität Erlangen-Nürnberg, Erlangen (DE)

(72) Inventors: Anja-Katrin Bosserhoff, Regensburg (DE); Alexander Riechers, Babensham (DE); Burkhard König, Lappersdorf (DE); Manuel Bause, Michelstadt (DE); Fabian Rauscher, Steinhöring (DE)

(73) Assignee: Friedrich-Alexander-Universität Erlangen-Nürnberg, Erlangen (DE)

( * ) Notice: Subject to any disclaimer, the term of this patent is extended or adjusted under 35 U.S.C. 154(b) by 0 days.

(21) Appl. No.: 15/580,062

(22) PCT Filed: May 24, 2016

(86) PCT No.: PCT/EP2016/061659
§ 371 (c)(1),
(2) Date: Dec. 6, 2017

(87) PCT Pub. No.: WO2016/198256
PCT Pub. Date: Dec. 15, 2016

(65) Prior Publication Data
US 2018/0280356 A1  Oct. 4, 2018

(30) Foreign Application Priority Data

Jun. 12, 2015  (EP) ..................... 15171966

(51) Int. Cl.
| | |
|---|---|
| *A61K 31/4184* | (2006.01) |
| *A61P 35/04* | (2006.01) |
| *A61K 9/00* | (2006.01) |
| *A61K 45/06* | (2006.01) |
| *A61K 31/138* | (2006.01) |
| *A61K 31/341* | (2006.01) |
| *A61K 31/4164* | (2006.01) |
| *A61K 31/4196* | (2006.01) |
| *A61K 31/426* | (2006.01) |
| *A61K 31/496* | (2006.01) |
| *A61K 31/497* | (2006.01) |
| *A61K 31/505* | (2006.01) |
| *A61K 31/513* | (2006.01) |
| *A61K 31/519* | (2006.01) |
| *A61K 31/53* | (2006.01) |
| *A61K 31/5375* | (2006.01) |
| *A61K 31/47* | (2006.01) |
| *A61K 31/435* | (2006.01) |
| *A61K 31/425* | (2006.01) |
| *A61K 31/381* | (2006.01) |
| *A61K 31/4985* | (2006.01) |
| *A61K 31/517* | (2006.01) |
| *A61K 31/197* | (2006.01) |
| *A61K 31/40* | (2006.01) |
| *A61K 31/4025* | (2006.01) |
| *A61K 31/4152* | (2006.01) |
| *A61K 31/4402* | (2006.01) |
| *A61K 31/4453* | (2006.01) |

(Continued)

(52) U.S. Cl.
CPC ........ *A61K 31/4184* (2013.01); *A61K 9/0053* (2013.01); *A61K 31/138* (2013.01); *A61K 31/197* (2013.01); *A61K 31/341* (2013.01); *A61K 31/381* (2013.01); *A61K 31/40* (2013.01); *A61K 31/4025* (2013.01); *A61K 31/4152* (2013.01); *A61K 31/4164* (2013.01); *A61K 31/4196* (2013.01); *A61K 31/425* (2013.01); *A61K 31/426* (2013.01); *A61K 31/435* (2013.01); *A61K 31/4402* (2013.01); *A61K 31/4453* (2013.01); *A61K 31/47* (2013.01); *A61K 31/472* (2013.01); *A61K 31/4704* (2013.01); *A61K 31/496* (2013.01); *A61K 31/497* (2013.01); *A61K 31/498* (2013.01); *A61K 31/4985* (2013.01); *A61K 31/501* (2013.01); *A61K 31/505* (2013.01); *A61K 31/506* (2013.01); *A61K 31/513* (2013.01); *A61K 31/517* (2013.01); *A61K 31/519* (2013.01); *A61K 31/52* (2013.01); *A61K 31/53* (2013.01); *A61K 31/5375* (2013.01); *A61K 31/5377* (2013.01); *A61K 31/55* (2013.01); *A61K 45/06* (2013.01); *A61P 35/04* (2018.01)

(58) Field of Classification Search
None
See application file for complete search history.

(56) References Cited

U.S. PATENT DOCUMENTS

2013/0095122 A1* 4/2013 Bosserhoff .............. A61P 19/04
424/174.1

FOREIGN PATENT DOCUMENTS

| CN | 101641097 A | 2/2010 |
|---|---|---|
| WO | 2005014812 A2 | 2/2005 |

(Continued)

OTHER PUBLICATIONS

Schafer et al. Drug Discovery Today, 2008, 13 (21/22), 913-916.*

(Continued)

*Primary Examiner* — Yong L Chu
(74) *Attorney, Agent, or Firm* — TraskBritt

(57) ABSTRACT

The present invention is directed to compounds, tautomers, stereoisomers, and chemically modified compounds thereof, and their use in preventing and/or treating tumors of metastasis and/or cartilage defect, and to a pharmaceutical composition comprising such compound.

21 Claims, 7 Drawing Sheets
Specification includes a Sequence Listing.

(51) Int. Cl.
| | | |
|---|---|---|
| *A61K 31/4704* | (2006.01) | |
| *A61K 31/472* | (2006.01) | |
| *A61K 31/498* | (2006.01) | |
| *A61K 31/501* | (2006.01) | |
| *A61K 31/506* | (2006.01) | |
| *A61K 31/52* | (2006.01) | |
| *A61K 31/5377* | (2006.01) | |
| *A61K 31/55* | (2006.01) | |

(56) References Cited

FOREIGN PATENT DOCUMENTS

| WO | 2005/105788 A1 | 11/2005 | |
|---|---|---|---|
| WO | 2008112509 A1 | 9/2008 | |
| WO | 2011113604 A1 | 9/2011 | |
| WO | WO-2011113604 A1 * | 9/2011 | ........... C07K 5/0812 |
| WO | 2016198256 A1 | 12/2016 | |

OTHER PUBLICATIONS

Hong et al. Journal of Translational Medicine 2004, 2(44), p. 1-8.*
Schmidt et al., Targeting Melanoma Metastasis and Immunosuppression with a New Mode of Melanoma Inhibitory Activity (MIA) Protein Inhibition, PLOS ONE, May 29, 2012, p. e37941, vol. 7, No. 5, 8 pages.
Balch et al., Prognostic Factors Analysis of 17,600 Melanoma Patients: Validation of the American Joint Committee on Cancer Melanoma Staging System, J. Clin Oncol., 2001, pp. 3622-3634, vol. 19.
Jachimczak et al., Inhibition of Immunosuppressive Effects of Melanoma-Inhibiting activity (MIA) by Antisense Techniques, Int. J. Cancer, 2005, pp. 88-92, vol. 113.
Lougheed et al., Structure of melanoma inhibitory activity protein, a member of a recently identified family of secreted proteins, PNAS, May 8, 2001, pp. 5515-5520, vol. 98, No. 10.
Lougheed et al., Solution structure and dynamics of melanoma inhibitory activity protein, Journal of Biomolecular NMR, 2002, pp. 211-223, vol. 22.
McArthur et al., Safety and efficacy of vemurafenib in BRAFV600E and BARFV600K mutation-positive melanoma (BRIM-3): extended follow-up of a phase 3, randomized, open-label study, Lancet Oncol, 2014, pp. 323-32, vol. 15.
Riechers et al., Heterogeneous transition metal-based fluorescence polarization (HTFP) assay for probing protein interactions, BioTechniques, Oct. 2009, pp. 837-844, vol. 47.
Schmid et al., Enhanced cartilage regeneration in MIA/CD-RAP deficient mice, Cell Death and Disease, 2010, 1, e97, doi:10.1038/cddis.2010.78.
Schmidt et al., MIA—a new target protein for malignant melanoma therapy, Histol Histopathol, Cellular and Molecular Biology, 2013, pp. 1-6.
Stoll et al., The extracellular human melanoma inhibitory activity (MIA) protein adopts an SH3 domain-like fold, The EMBO Journal, 2001, pp. 340-349, vol. 20, No. 3.
Stoll et al., Detailed analysis of MIA protein by mutagenesis, Biol. Chem., Dec. 2006, pp. 1601-1606, vol. 387.
International Written Opinion for International Application No. PCT/EP16/061659, dated Aug. 10, 2016, 5 pages.
International Search Report for International Application No. PCT/EP2016/061659, dated Aug. 10, 2016, 4 pages.
European Communication pursuant to Article 94(3) EPC for European Application No. 16725108.1, dated Jan. 14, 2019, 3 pages.
European Search and Opinion for European Application No. 15171966, dated Dec. 14, 2015, 7 pages.
Chinese First Office Action and Search Report for Chinese Application No. 201680041276.1, dated Mar. 11, 2020, 16 pages with translation.
STN-Registry Nos. 213251-08-2 (Published Oct. 27, 1998); 1351647-28-3 (Published Nov. 17, 2005); 868229-05-4 (Published Dec. 22, 2011) 2 pages.

* cited by examiner

Fig. 1: Model of MIA dimer forming dimerization (binding) site
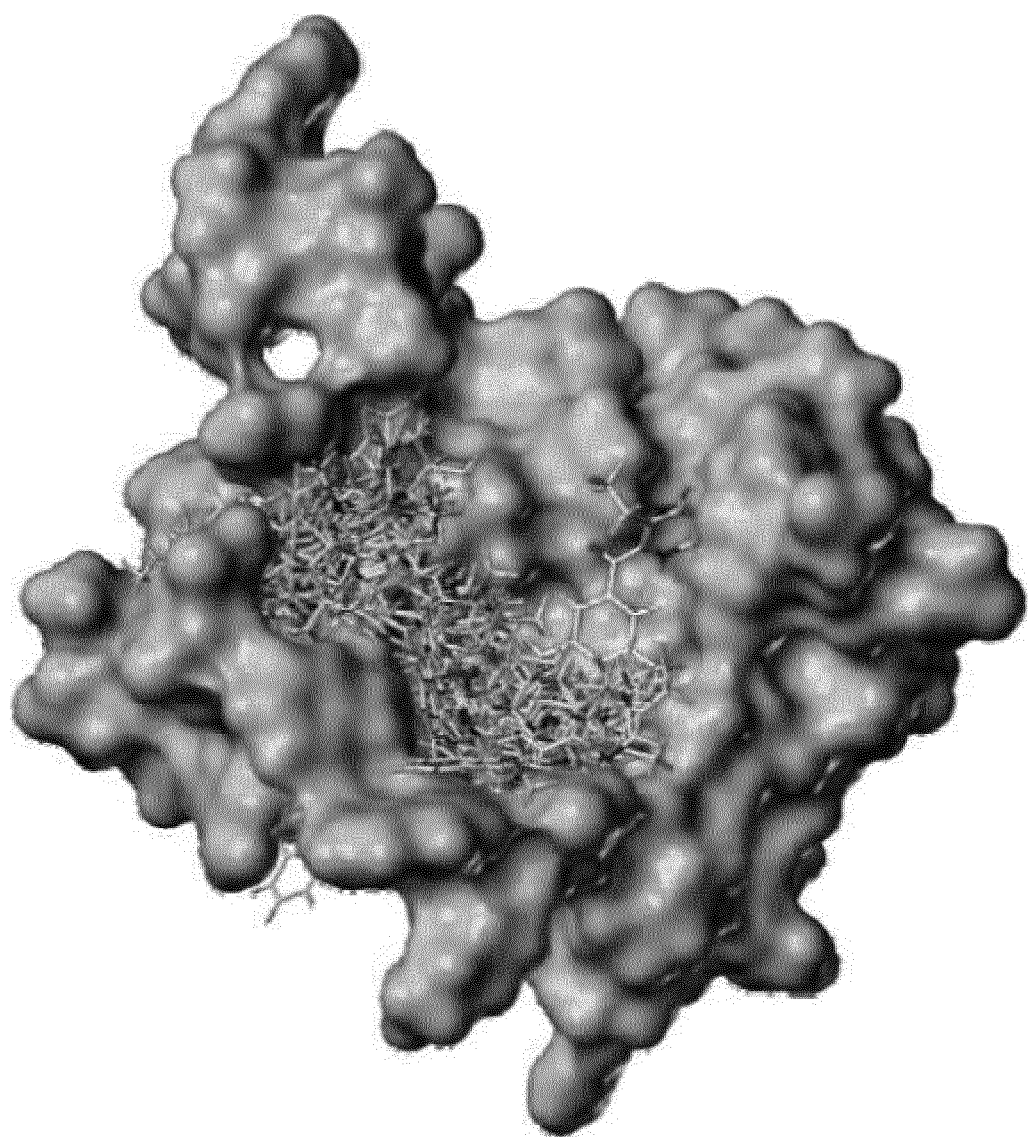

Fig. 2A: Predicted passing of the blood-brain-barrier of compound 3
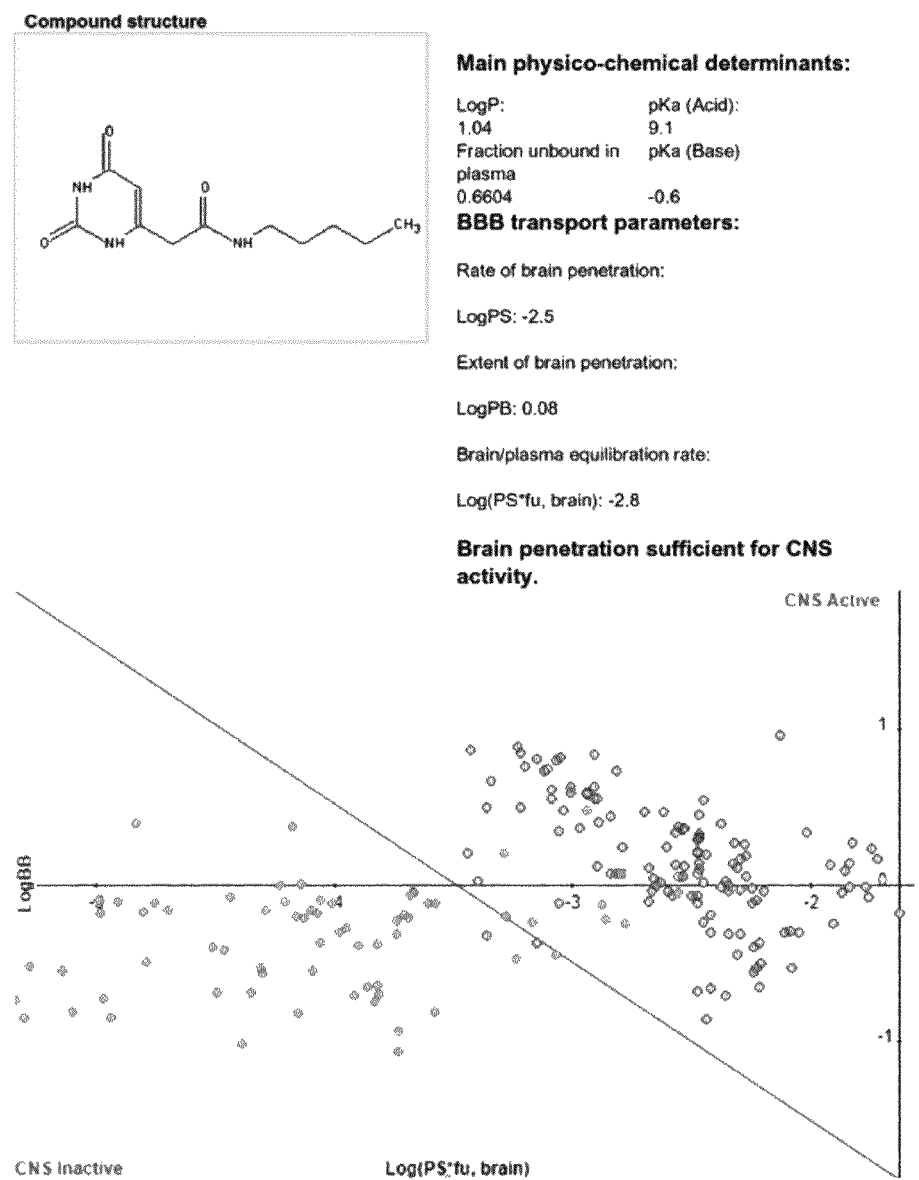

Fig. 2B: Predicted oral availability of compound 3
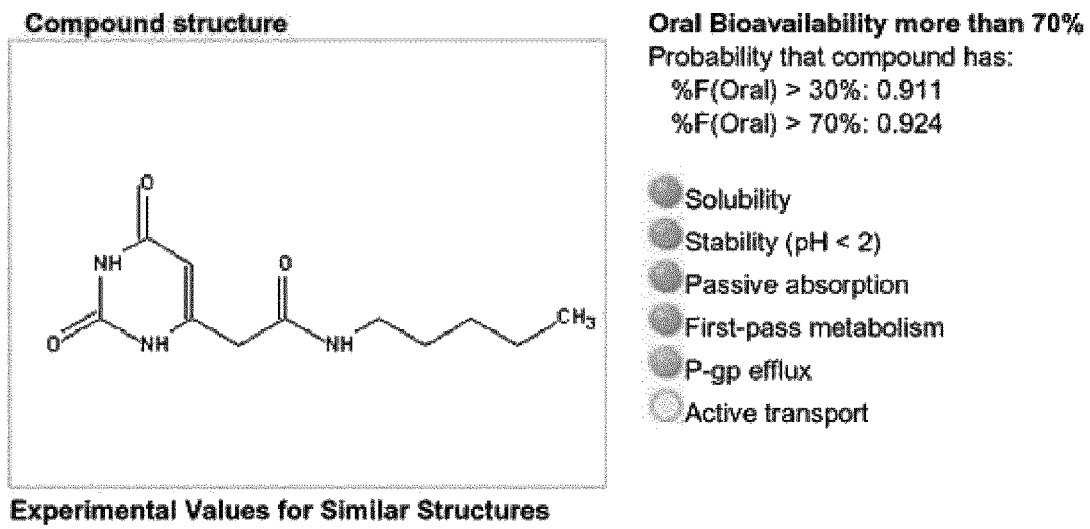
Fig. 2C: Predicted systemic toxicity of compound 3
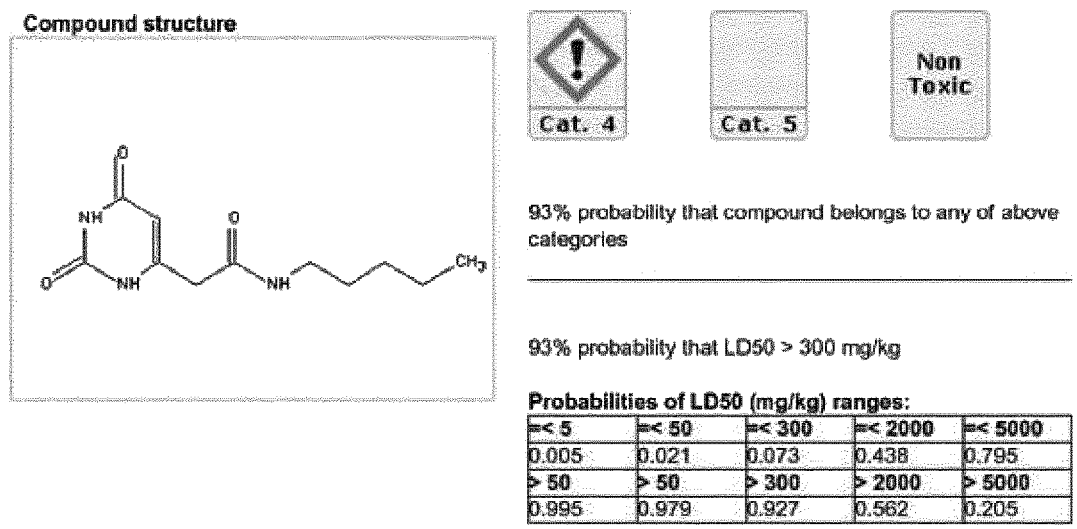

Fig. 3: Inhibition of MIA dimerization measured in HTFP assay
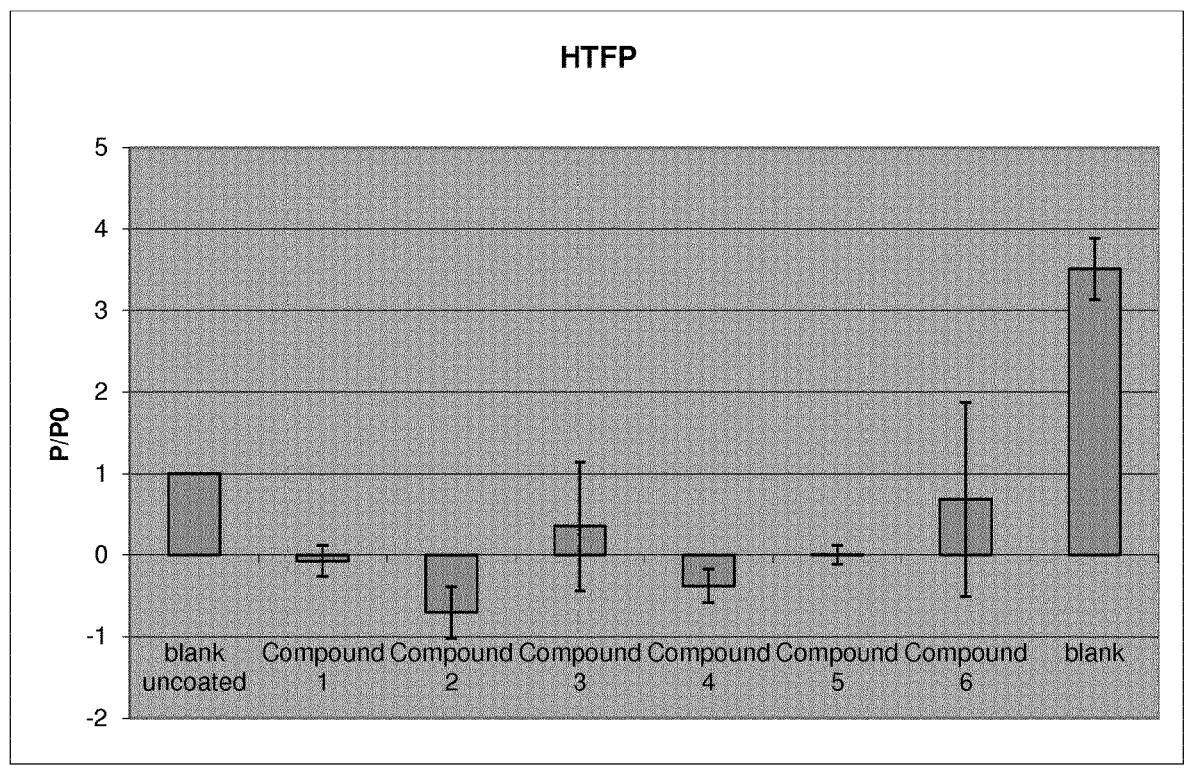

Fig. 4: Inhibition of MIA activity
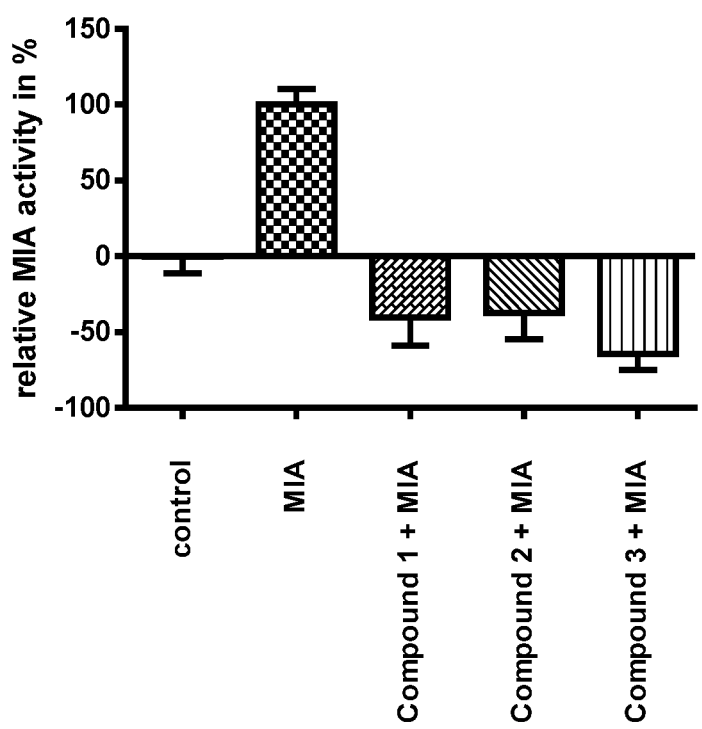

Fig. 5A and 5B: Effect of compounds 1 to 6 on fibroblasts
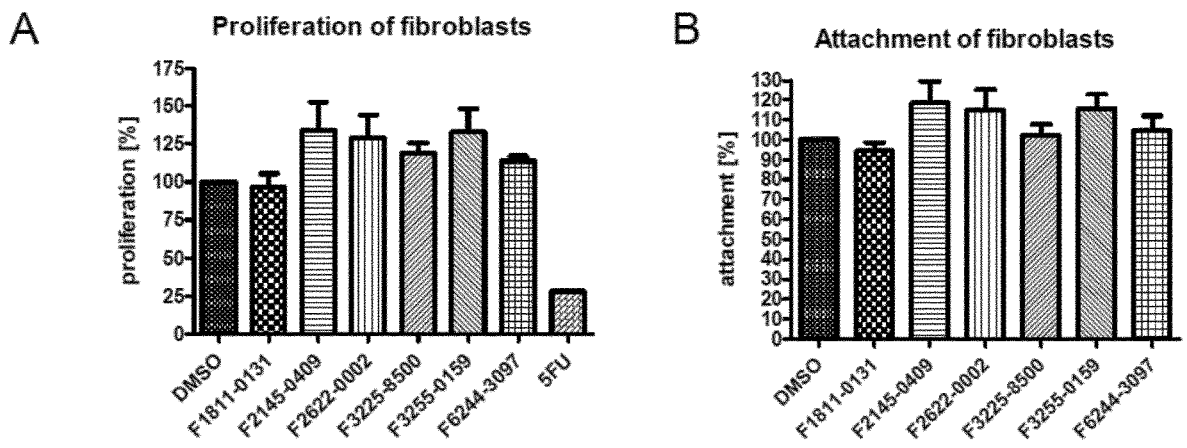
Fig. 5C and 5D: Effect of compounds 1 to 6 on kidney cells
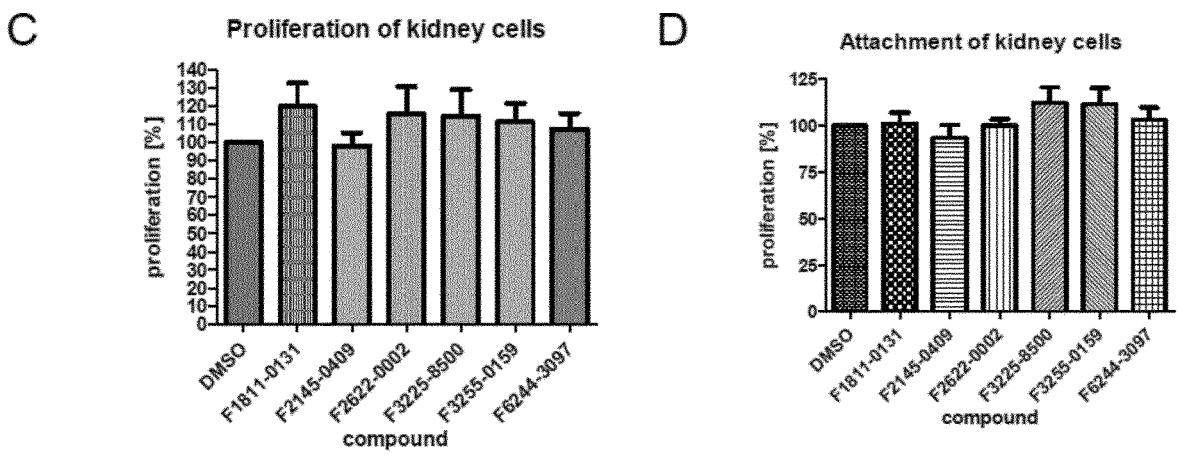

Fig. 6: Effect of compound 1 on proliferation of melanoma cells
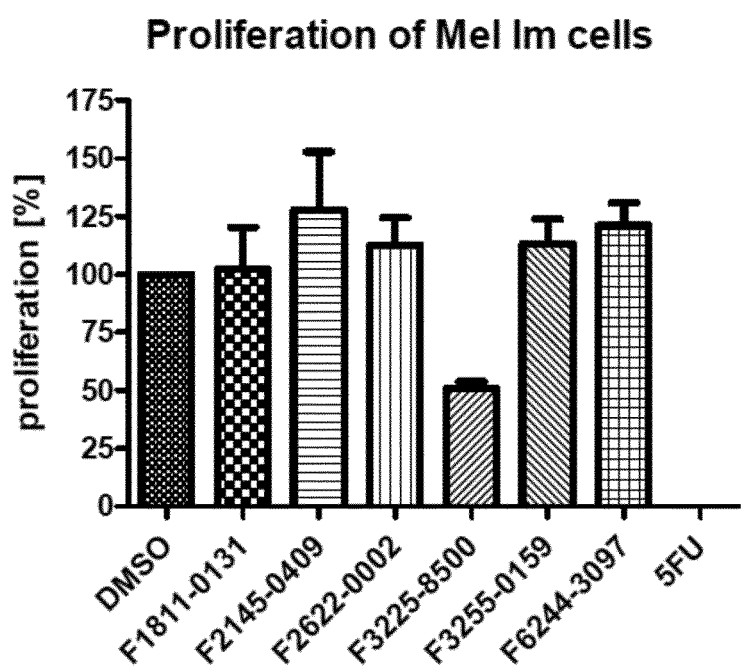

NON-HYDROPHOBIC COMPOUNDS FOR USE IN TREATING METASTASIS AND/OR CARTILAGE DEFECT

CROSS-REFERENCE TO RELATED APPLICATIONS

This application is a national phase entry under 35 U.S.C. § 371 of International Patent Application PCT/EP2016/061659, filed May 24, 2016, designating the United States of America and published in English as International Patent Publication WO 2016/198256 A1 on Dec. 15, 2016, which claims the benefit under Article 8 of the Patent Cooperation Treaty to European Patent Application Serial No. 15171966.3, filed Jun. 12, 2015.

The present invention refers to non-hydrophobic compounds, their use in prevention and/or treatment of metastasis and/or cartilage defect, and to a pharmaceutical composition comprising such compound, wherein the compound or composition is for example administered orally.

TECHNICAL BACKGROUND

Malignant melanoma is the skin cancer with the highest mortality rate. It is characterized by an early onset of metastasis formation and rapid disease progression; in the case of systemic metastases the 5-year survival rate is less than 10% (Balch, C. M., et al., *Prognostic Factors Analysis of 17,600 Melanoma Patients: Validation of the American Joint Committee on Cancer Melanoma Staging System.* Journal of Clinical Oncology, 2001. 19(16): p. 3622-3634). In the TopS-EU-countries (Germany, UK, France, Spain, Italy), USA and Australia 125.000 incidences of primary tumors have been diagnosed in the year 2010; until 2025 an increase of 150.000 is expected (Globocan 2008). With the incidence of this malignancy increasing, new therapeutic attempts are simultaneously emerging. They include the BRAF V600E inhibitor Vemurafenib, the c-Kit inhibitor Imatinib, the anti-CTLA-4 antibody Ipilimumab, which activates the immune system, as well as anti-PD1 immune checkpoint inhibitors Nivolumab and Lambrolizumab; however, overall survival remains poor (McArthur, G. A., et al., *Safety and efficacy of vemurafenib in BRAFV600E and BRAFV600K mutation-positive melanoma (BRIM-3): extended follow-up of a phase 3, randomised, open-label study.* The Lancet Oncology, 2014. 15(3): p. 323-332).

MIA, an 11 kDa protein secreted by melanocytic tumor cells, has been linked to cellular migration and invasion, which leads to the formation of metastases. It has also been associated with immunosuppression of malignant melanoma (Jachimczak, P., et al., *Inhibition of immunosuppressive effects of melanoma-inhibiting activity (MIA) by antisense techniques.* International Journal of Cancer, 2005. 113(1): p. 88-92) and is a diagnostic serum marker for melanoma disease progression as it is barely expressed in healthy tissue except by differentiating chondrocytes. MIA, also known as CD-RAP (cartilage-derived retinoic acid-sensitive protein), is not only expressed in melanoma cells but also in chondrocytes and modulates regeneration of regeneration of defect cartilage (Schmid R, Schiffner S, Opolka A, Grässel S, Schubert T, Moser M, Bosserhoff A K. Cell Death Dis. 2010 Nov. 11). Analysis of the MIA/CD-RAP-knockout-mouse revealed that MIA/CD-RAP influences interactions between chondrocytes and their surrounding extracellular matrix, inhibits the proliferation of mesenchymal cells and promotes chondrocyte differentiation MIA is not only expressed in the context of melanoma but in numerous types of tumors, often late stage tumors such as breast cancer, glioma, pancreas carcinoma, and colon carcinoma etc. MIA allows the release of cells from the tumor by masking of binding sites for fibronectin and/or integrin and their migration in one direction which results in the invasion into other tissues and the formation of metastasis.

In WO 2011/113604 it is disclosed that MIA is functionally active as a homodimeric species and that peptides, e.g., AR71, are able to block the MIA-MIA interaction and in consequence to inhibit the formation of metastases and/or influence, cartilage formation, e.g., chondrocyte differentiation. No adverse effects were observed after a peptide treatment of mice. However, peptides generally make for poor drug candidates as they are readily degraded by proteases in the digestive tract or in the serum and are therefore typically not orally available.

Hence, the present invention is dirceted to improved inhibitors of the MIA dimerization for effective use in the prevention and/or treatment of metastasis and/or cartilage defect, which are for example even orally administrable.

SUMMARY

In the present invention compounds have been investigated which are non-hydrophobic and interact with the dimerization site of MIA comprising or formed by for example at least three amino acid residues of the MIA protein selected from cysteine 17, serine 18, tyrosine 47, glycine 61, glycine 66, aspartate 67, leucine 76, tryptophan 102, aspartate 103, cysteine 106, valine 64, tyrosine 69, aspartate 87, lysine 91, glycine 54, leucine 58, phenylalanine 59, alanine 7, lysine 53, arginine 55, arginine 57, arginine 85 and lysine 94. Alternatively the dimerization site is selected from cysteine 17, serine 18, tyrosine 47, glycine 61, glycine 66, aspartate 67, leucine 76, tryptophan 102, aspartate 103, cysteine 106, alanine 7, lysine 53, arginine 55, arginine 57, arginine 85, and lysine 94. A further selection is for example cysteine 17, serine 18, tyrosine 47, glycine 61, glycine 66, aspartate 67, leucine 76, tryptophan 102, aspartate 103 and cysteine 106.

The non-hydrophobic compounds are used alone or in combination for use in preventing and/or treating metastasis caused by the dimerization of MIA protein and/or a cartilage defect, wherein regeneration is inhibited by MIA dimerization, wherein the compound(s) is/are selected from the group consisting of compound 1 to 270 of Table 1, tautomers, stereoisomers as well as chemically modified compounds thereof.

The metastasis preventable and/or treatable by the compounds of the present invention is based on any primary tumor expressing MIA such as melanoma, breast cancer, glioma, pancreas carcinoma, colon carcinoma, etc. The metastasis is located for example in the liver, lung, bone, colon, stomach, nerves, lymph nodes, skin and/or brain.

The compound of the present invention is administered alone or in combination with other non-hydrophobic compounds of the present invention, and in combination with a chemotherapeutic (e.g., Vermurafenib, Ipilimumab, Trametinib, Dabradenib, Dacarbazine, Paclitaxel, Carboplatin, Interferon-alpha, Aldesleukin etc.) comprising for example also an inhibitory cytokine (e.g., TGF alpha, TGF beta, interleukin etc.).

The compounds are either administered at the same time or consecutively.

The present invention is further directed to a pharmaceutical composition comprising one or more compounds of the present invention for use in preventing and/or treating of metastasis caused by the dimerization of melanoma inhibitory activity (MIA) protein and/or a cartilage defect, wherein regeneration is inhibited by MIA dimerization, wherein the pharmaceutical composition comprises at least one compound selected from the group consisting of compound 1 to 270 of Table 1, tautomers, stereoisomers and chemically modified compounds thereof, and a pharmaceutically acceptable carrier and/or solvent and optionally a chemotherapeutic.

In one embodiment the compound or the pharmaceutical composition of the present invention is administered orally.

FIG. 1 depicts a model of a MIA dimer wherein compounds of the present invention are bound to the MIA-MIA interaction site, also called MIA dimerization site.

FIG. 2 shows predicted passing of the blood-brain-barrier (FIG. 2A), predicted oral availability (FIG. 2B) and predicted systemic toxicity (FIG. 2C) of compound 3 (F1811-0131).

FIG. 3 presents inhibition of MIA dimerization by compounds 1 to 6 measured in the HTFP assay.

FIG. 4 shows Boyden chamber assays demonstrating the inhibition of melanoma cell migration by compounds 1, 2 and 3, respectively.

FIG. 5 depicts compounds 1 to 6 tested on proliferation and attachment of fibroblasts (FIG. 5A, 5B) and kidney cells HEK-293 (FIG. 5C, 5D), respectively. None of the tested compounds has an effect on these cells.

FIG. 6 presents the inhibition of the proliferation of the melanoma cell Mel-Im line by compound 1.

DETAILED DESCRIPTION

As a general treatment concept, the selective inhibition of MIA dimerization is an attractive therapy concept since, apart from its expression in malignant melanoma, MIA is only expressed by differentiating chondrocytes. Furthermore, the inhibition strategy of the present invention targets secreted extracellular MIA; thus the need for cell permeability of the compounds of the present invention is avoided. The compounds of the present invention are specifically developed and used for preventing and/or treating metastasis caused by the dimerization of melanoma inhibitory activity (MIA) protein or a cartilage defect which results for example in mechanical or immunological destruction and suppression of regeneration of the cartilage by MIA dimerization. MIA avoids the dedifferentiation of chondrocytes which would allow the proliferation of the chondrocytes. Without (dimerized) MIA, the chondrocytes transform into a certain type of precursor cells which are ale to grow and to regenerate, i.e., close a cartilage defect. MIA blocks this regeneration.

The compounds of the present invention interact and bind respectively, with/to the dimerization site of MIA proteins. Thus, the compounds of the present invention avoid the dimerization of MIA proteins and/or break up existing MIA dimers.

The MIA dimerization site which is the site where MIA proteins interact comprises or is formed by at least three amino acid residues of said MIA protein selected from cysteine 17, serine 18, tyrosine 47, glycine 61, glycine 66, aspartate 67, leucine 76, tryptophan 102, aspartate 103, cysteine 106, valine 64, tyrosine 69, aspartate 87, lysine 91, glycine 54, leucine 58, phenylalanine 59, alanine 7, lysine 53, arginine 55, arginine 57, arginine 85 and lysine 94. In one embodiment, the dimerization site of a MIA protein comprises or consists of cysteine 17, serine 18, tyrosine 47, glycine 61, glycine 66, aspartate 67, leucine 76, tryptophan 102, aspartate 103, cysteine 106, alanine 7, lysine 53, arginine 55, arginine 57, arginine 85, and lysine 94. In another embodiment, the MIA dimerization site comprises or consists of cysteine 17, serine 18, tyrosine 47, glycine 61, glycine 66, aspartate 67, leucine 76, tryptophan 102, aspartate 103 and cysteine 106.

Via the dimerization site even more than two MIA proteins may interact and form an aggregate comprising or consisting of three or more MIA proteins. FIG. 1 presents a model of such MIA dimerization site virtually bound to numerous compounds of the present invention. The amino acids of the MIA protein forming the dimerization site are hydrophobic in that the dimerization site is hydrophobic. Surprisingly, the compounds of the present invention interacting with the MIA dimerization site are non-hydrophobic. The compounds of the present invention for use in preventing and/or treating metastasis caused by the dimerization of MIA protein or a cartilage defect are listed in the following Table 1. The invention further comprises the tautomers, stereoisomers and chemically modified compounds of the compounds listed in Table 1.

TABLE 1

| Compound x | Structure | No. | Tautomere/Stereoisomer | Reference of Variant |
|---|---|---|---|---|
| Compound 1 | [structure: 5-amino-4-(1H-1,3-benzodiazol-2-yl)-1-(butan-2-yl)-2,3-dihydro-1H-pyrrol-3-one] Preferred IUPAC Name = 5-amino-4-(1H-1,3-benzodiazol-2-yl)-1-(butan-2-yl)-2,3-dihydro-1H-pyrrol-3-one | F3225-8500 | [tautomer structure] | F3225-8500_8_2 (1 of 28) |

TABLE 1-continued

| Compound x | Structure | No. | Tautomere/Stereoisomer | Reference of Variant |
|---|---|---|---|---|
| Compound 2 | Preferred IUPAC Name = N-[4-(1,2,3,4-tetrahydroisoquinolin-2-yl)but-2-yn-1-yl]methanesulfonamide | F6244-3097 | | F6244-3097_1 (1 of 2) |
| Compound 3 | Preferred IUPAC Name = 2-(2,6-dioxo-1,2,3,6-tetrahydropyrimidin-4-yl)-N-Pentylacetamide | F1811-0131 | | F1811-0131_52_1 (1 of 76) |
| Compound 4 | Preferred IUPAC Name = 1-{1-[2-hydroxy-3-(piperazin-1-yl)propyl]-2,4-dimethyl-1H-pyrrol-3-yl}ethan-1-one | F3255-0159 | | F3255-0159_3_2 (1 of 8) |
| Compound 5 | Preferred IUPAC Name = 5-methoxy-2-(piperazin-1-ylmethyl)-1H-1,3-Benzodiazole | F2145-0409 | | F2145-0409_5_1 (1 of 14) |
| Compound 6 | Preferred IUPAC Name = N-butyl-2-hydroxy-9-methyl-4-oxo-4H-pyrido[1,2-a]pyrimidine-3-carboxamide | F2622-0002 | | F2622-0002_7_1 (1 of 40) |

TABLE 1-continued

| Compound x | Structure | No. | Tautomere/Stereoisomer | Reference of Variant |
|---|---|---|---|---|
| Compound 7 | 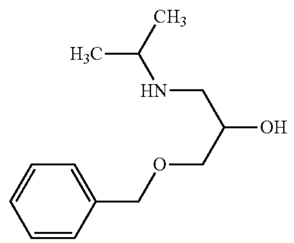 [SMILES: CC(C)NCC(O)COCc1ccccc1] | F0050-0006 | | F0050-0006_2 (1 of 4) |
| Compound 8 | 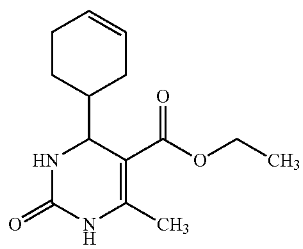 [SMILES: CCOC(=O)C1=C(C)NC(=O)NC1C1CC=CCC1] | F0095-1317 | | F0095-1317_13_5 (1 of 116) |
| Compound 9 | 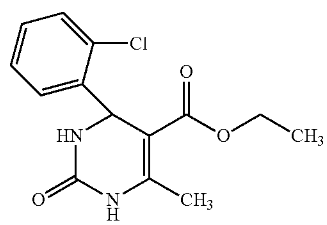 [SMILES: CCOC(=O)C1=C(C)NC(=O)NC1c1ccccc1Cl] | F0126-0203 | | F0126-0203_16_4 (1 of 46) |
| Compound 10 | 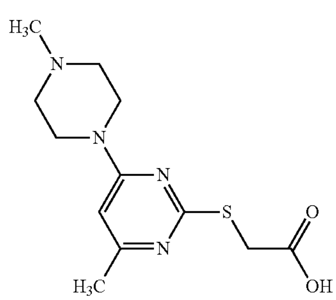 [SMILES: Cc1cc(N2CCN(C)CC2)nc(SCC(=O)O)n1] | F0176-0083 | | F0176-0083_3_1 (1 of 10) |
| Compound 11 | 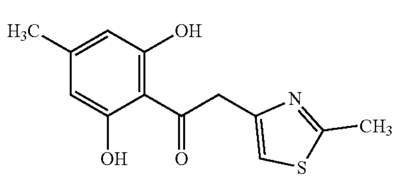 | F0196-0408 | | F0196-0408_1_1 (1 of 2) |

TABLE 1-continued

| Compound x | Structure | No. | Tautomere/Stereoisomer | Reference of Variant |
|---|---|---|---|---|
| Compound 12 | 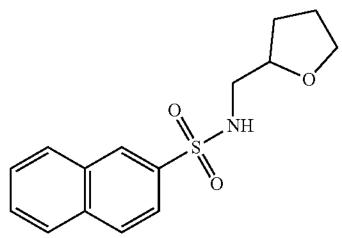 [SMILES: O=S(=O)(NCC1CCCO1)c1ccc2ccccc2c1] | F0285-0322 | | F0285-0322_2 (1 of 2) |
| Compound 13 | 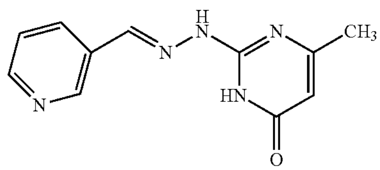 [SMILES: Cc1cc(=O)[nH]c(N/N=C/c2cccnc2)n1] | F0347-0341 | | F0347-0341_21_1 (1 of 14) |
| Compound 14 | 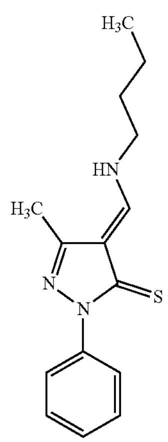 [SMILES: CCCCN/C=C1/C(=S)N(c2ccccc2)N=C1C] | F0347-0841 | | F0347-0841_18_1 (1 of 12) |
| Compound 15 | 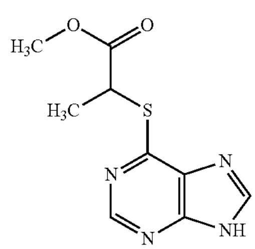 [SMILES: COC(=O)C(C)Sc1ncnc2[nH]cnc12] | F0578-0190 | | F0578-0190_7_1 (1 of 22) |
| Compound 16 | 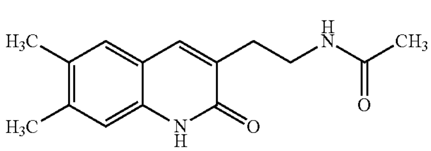 [SMILES: CC(=O)NCCc1cc2cc(C)c(C)cc2[nH]c1=O] | F0611-0055 | | F0611-0055_1 (1 of 4) |

TABLE 1-continued

| Compound x | Structure | No. | Tautomere/Stereoisomer | Reference of Variant |
|---|---|---|---|---|
| Compound 17 | 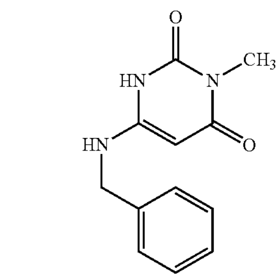 [SMILES: Cn1c(=O)cc(NCc2ccccc2)[nH]c1=O] | F0693-0722 | | F0693-0722_14_1 (1 of 22) |
| Compound 18 | 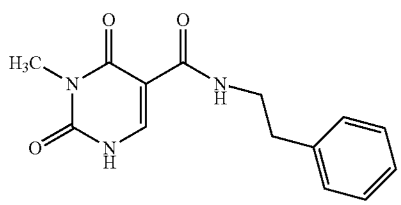 [SMILES: Cn1c(=O)[nH]cc(C(=O)NCCc2ccccc2)c1=O] | F0696-0806 | | F0696-0806_6_1 (1 of 44) |
| Compound 19 | 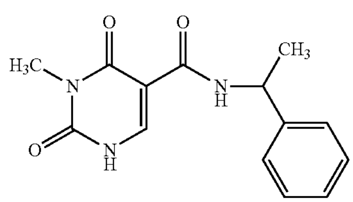 [SMILES: CC(NC(=O)c1c[nH]c(=O)n(C)c1=O)c1ccccc1] | F0696-0849 | | F0696-0849_24_1 (1 of 88) |
| Compound 20 | 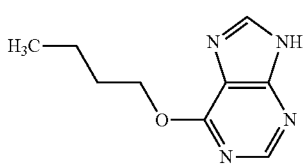 | F0704-0019 | | F0704-0019_7_1 (1 of 11) |
| Compound 21 | 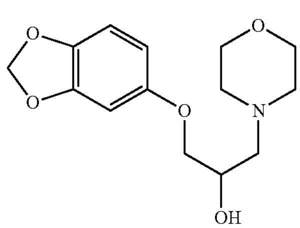 [SMILES: OC(COc1ccc2c(c1)OCO2)CN1CCOCC1] | F0719-0066 | | F0719-0066_1 (1 of 4) |
| Compound 22 | 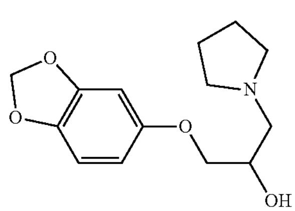 [SMILES: OC(COc1ccc2c(c1)OCO2)CN1CCCC1] | F0719-0070 | | F0719-0070_1_1 (1 of 4) |

TABLE 1-continued

| Compound x | Structure | No. | Tautomere/Stereoisomer | Reference of Variant |
|---|---|---|---|---|
| Compound 23 | 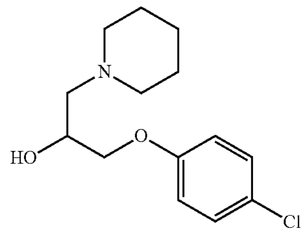 [SMILES: OC(COc1ccc(Cl)cc1)CN1CCCCC1] | F0719-0145 | | F0719-0145_1_1 (1 of 4) |
| Compound 24 | 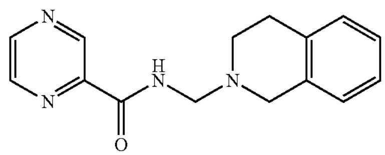 [SMILES: O=C(NCN1CCc2ccccc2C1)c1cnccn1] | F0815-0092 | | F0815-0092_1_1 (1 of 7) |
| Compound 25 | 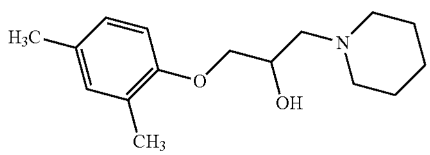 | F0840-0033 | | F0840-0033_2 (1 of 4) |
| Compound 26 | 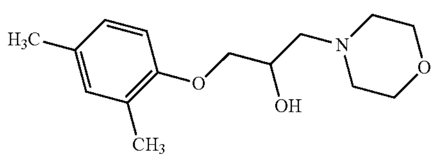 [SMILES: Cc1ccc(OCC(O)CN2CCOCC2)c(C)c1] | F0840-0034 | | F0840-0034_1_1 (1 of 4) |
| Compound 27 | 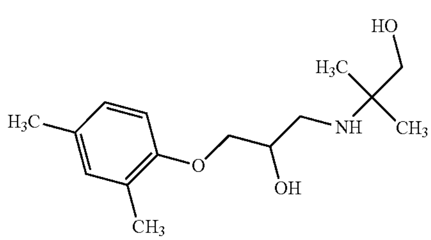 [SMILES: Cc1ccc(OCC(O)CNC(C)(C)CO)c(C)c1] | F0840-0058 | | F0840-0058_1 (1 of 4) |
| Compound 28 | 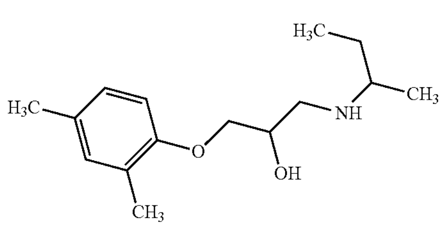 [SMILES: CCC(C)NCC(O)COc1ccc(C)cc1C] | F0840-0059 | | F0840-0059_1 (1 of 8) |

TABLE 1-continued

| Compound x | Structure | No. | Tautomere/Stereoisomer | Reference of Variant |
|---|---|---|---|---|
| Compound 29 | 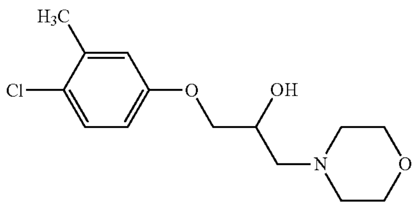 [SMILES: Cc1cc(OCC(O)CN2CCOCC2)ccc1Cl] | F0840-0204 | | F0840-0204_1_2 (1 of 4) |
| Compound 30 | 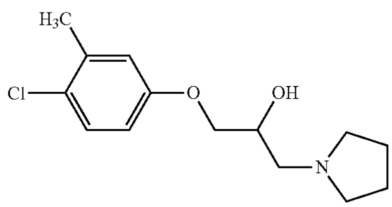 [SMILES: Cc1cc(OCC(O)CN2CCCC2)ccc1Cl] | F0840-0206 | | F0840-0206_2 (1 of 4) |
| Compound 31 | 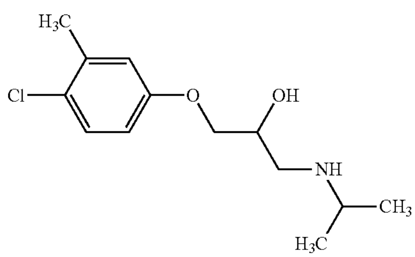 [SMILES: Cc1cc(OCC(O)CNC(C)C)ccc1Cl] | F0840-0214 | | F0840-0214_2 (1 of 4) |
| Compound 32 | 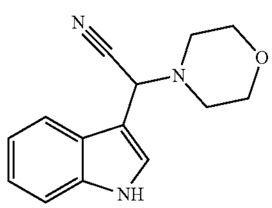 [SMILES: N#CC(c1c[nH]c2ccccc12)N1CCOCC1] | F0896-0201 | | F0896-0201_1_2 (1 of 4) |
| Compound 33 | 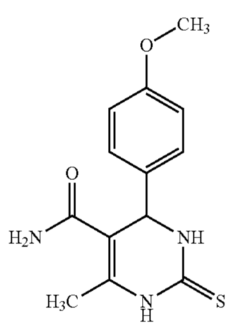 [SMILES: COc1ccc(C2NC(=S)NC(C)=C2C(N)=O)cc1] | F0910-6535 | | F0910-6535_23_1 (1 of 124) |
| Compound 34 | 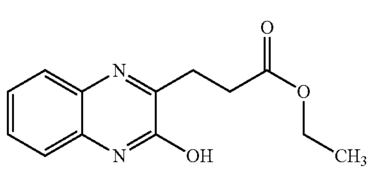 [SMILES: CCOC(=O)CCc1nc2ccccc2nc1O] | F0915-2932 | | F0915-2932_3_1 (1 of 8) |

TABLE 1-continued

| Compound x | Structure | No. | Tautomere/Stereoisomer | Reference of Variant |
|---|---|---|---|---|
| Compound 35 | 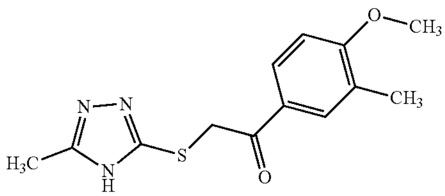 | F0915-2972 | | F0915-2972_3_1 (1 of 5) |
| Compound 36 | 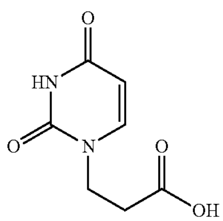 [SMILES: O=C(O)CCn1ccc(=O)[nH]c1=O] | F0918-1472 | | F0918-1472_8_1 (1 of 10) |
| Compound 37 | 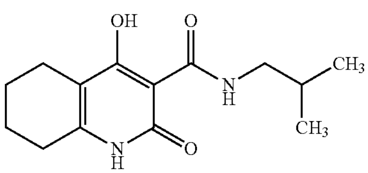 [SMILES: CC(C)CNC(=O)c1c(O)c2c([nH]c1=O)CCCC2] | F0919-7794 | | F0919-7794_104_3 (1 of 270) |
| Compound 38 | 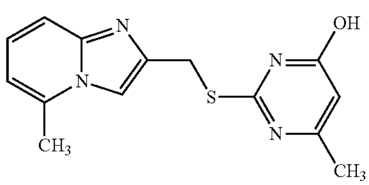 [SMILES: Cc1cc(O)nc(SCc2cn3c(C)cccc3n2)n1] | F1001-0002 | | F1001-0002_5_1 (1 of 12) |
| Compound 39 | 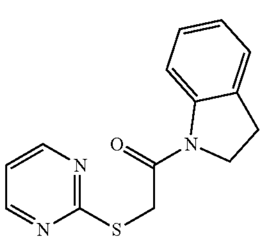 [SMILES: O=C(CSc1ncccn1)N1CCc2ccccc21] | F1016-0141 | | F1016-0141_1_1 (1 of 2) |

TABLE 1-continued

| Compound x | Structure | No. | Tautomere/Stereoisomer | Reference of Variant |
|---|---|---|---|---|
| Compound 40 | 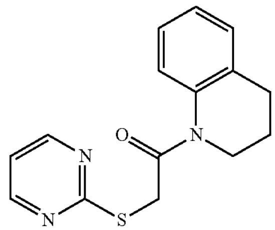 [SMILES: O=C(CSc1ncccn1)N1CCCc2ccccc21] | F1016-0159 | | F1016-0159_1_1 (1 of 2) |
| Compound 41 | 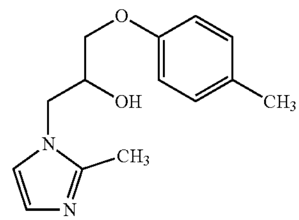 [SMILES: Cc1ccc(OCC(O)Cn2ccnc2C)cc1] | F1021-0224 | | F1021-0224_1_2 (1 of 4) |
| Compound 42 | 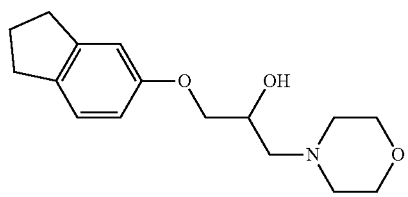 [SMILES: OC(COc1ccc2c(c1)CCC2)CN1CCOCC1] | F1032-0001 | | F1032-0001_1_2 (1 of 4) |
| Compound 43 | 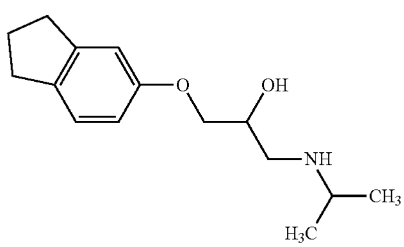 [SMILES: CC(C)NCC(O)COc1ccc2c(c1)CCC2] | F1032-0021 | | F1032-0021_1_2 (1 of 4) |
| Compound 44 | 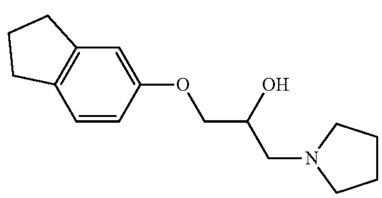 [SMILES: OC(COc1ccc2c(c1)CCC2)CN1CCCC1] | F1032-0031 | | F1032-0031_1 (1 of 4) |
| Compound 45 | 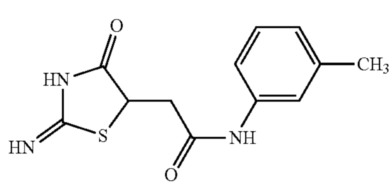 [SMILES: Cc1cccc(NC(=O)CC2SC(=N)NC2=O)c1] | F1065-0751 | | F1065-0751_3_1 (1 of 8) |

TABLE 1-continued

| Compound x | Structure | No. | Tautomere/Stereoisomer | Reference of Variant |
|---|---|---|---|---|
| Compound 46 | 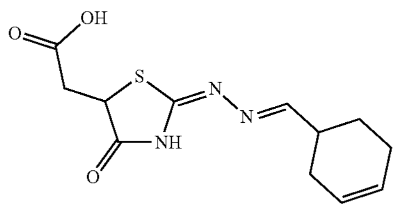 [SMILES: O=C(O)CC1S/C(=N/N=C/C2CC=CCC2)NC1=O] | F1107-0031 | | F1107-0031_80_4 (1 of 448) |
| Compound 47 | 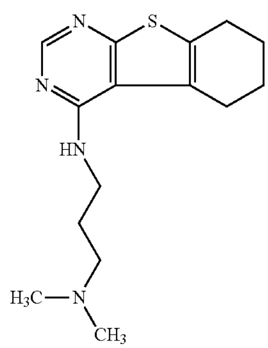 [SMILES: CN(C)CCCNc1ncnc2sc3c(c12)CCCC3] | F1126-0569 | | F1126-0569_4_1 (1 of 6) |
| Compound 48 | 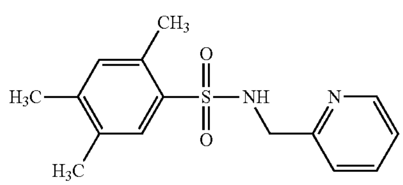 [SMILES: Cc1cc(C)c(S(=O)(=O)NCc2ccccn2)cc1C] | F1132-0388 | | F1132-0388_1_1 (1 of 1) |
| Compound 49 | 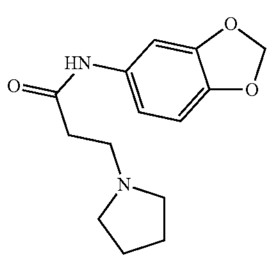 [SMILES: O=C(CCN1CCCC1)Nc1ccc2c(c1)OCO2] | F1174-1011 | | F1174-1011_1_1 (1 of 2) |
| Compound 50 | 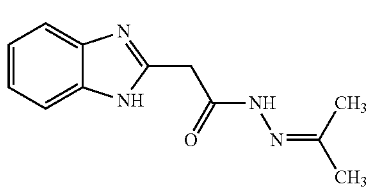 [SMILES: CC(C)=NNC(=O)Cc1nc2ccccc2[nH]1] | F1243-0186 | | F1243-0186_3_1 (1 of 6) |

TABLE 1-continued

| Compound x | Structure | No. | Tautomere/Stereoisomer | Reference of Variant |
|---|---|---|---|---|
| Compound 51 | 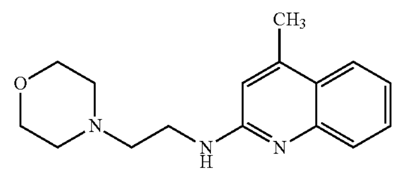 [SMILES: Cc1cc(NCCN2CCOCC2)nc2ccccc12] | F1360-0381 | | F1360-0381_3_1 (1 of 4) |
| Compound 52 | 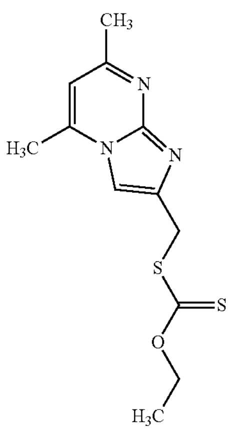 [SMILES: CCOC(=S)SCc1cn2c(C)cc(C)nc2n1] | F1387-0270 | | F1387-0270_2_1 (1 of 3) |
| Compound 53 | 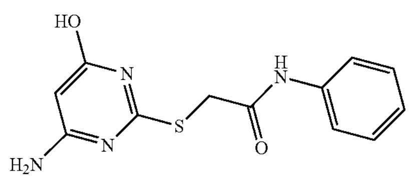 [SMILES: Nc1cc(O)nc(SCC(=O)Nc2ccccc2)n1] | F1411-0031 | | F1411-0031_9_1 (1 of 14) |
| Compound 54 | 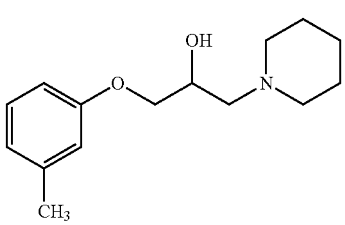 [SMILES: Cc1cccc(OCC(O)CN2CCCCC2)c1] | F1438-0002 | | F1438-0002_2 (1 of 4) |
| Compound 55 | 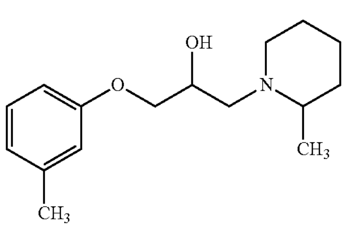 [SMILES: Cc1cccc(OCC(O)CN2CCCCC2C)c1] | F1438-0006 | | F1438-0006_1_3 (1 of 8) |

TABLE 1-continued

| Compound x | Structure | No. | Tautomere/Stereoisomer | Reference of Variant |
|---|---|---|---|---|
| Compound 56 | 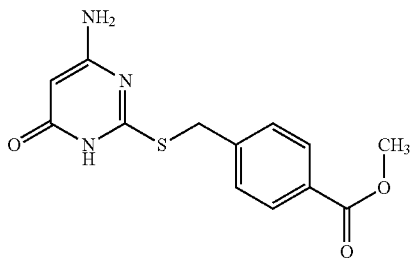 [SMILES: COC(=O)c1ccc(CSc2nc(N)cc(=O)[nH]2)cc1] | F1440-0010 | | F1440-0010_9_1 (1 of 14) |
| Compound 57 | 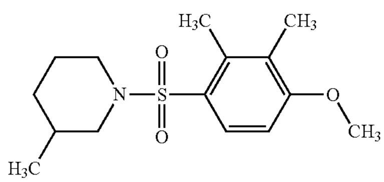 [SMILES: COc1ccc(S(=O)(=O)N2CCCC(C)C2)c(C)c1C] | F1478-0152 | | F1478-0152_1 (1 of 2) |
| Compound 58 | 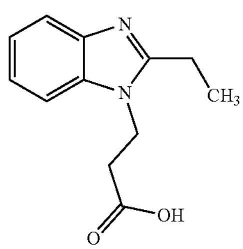 [SMILES: CCc1nc2ccccc2n1CCC(=O)O] | F1501-0026 | | F1501-0026_1 (1 of 4) |
| Compound 59 | 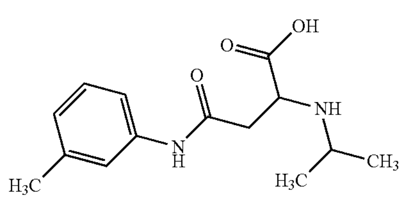 [SMILES: Cc1cccc(NC(=O)CC(NC(C)C)C(=O)O)c1] | F1533-0056 | | F1533-0056_2_2 (1 of 8) |
| Compound 60 | 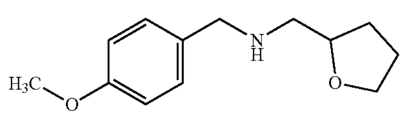 [SMILES: COc1ccc(CNCC2CCCO2)cc1] | F1549-0007 | | F1549-0007_1_1 (1 of 4) |

TABLE 1-continued
| Compound x | Structure | No. | Tautomere/Stereoisomer | Reference of Variant |
|---|---|---|---|---|
| Compound 61 | 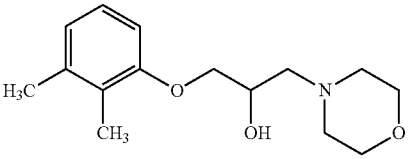 [SMILES: Cc1cccc(OCC(O)CN2CCOCC2)c1C] | F1562-0050 | 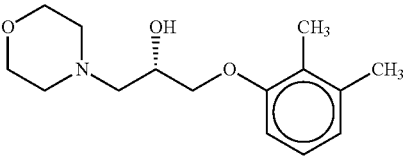 | F1562-0050_1 (1 of 4) |
| Compound 62 | 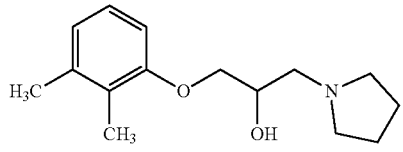 | F1562-0059 | 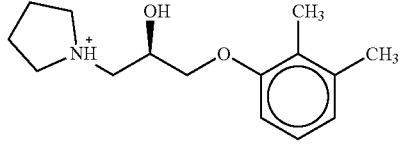 | F1562-0059_1_2 (1 of 4) |
| Compound 63 | 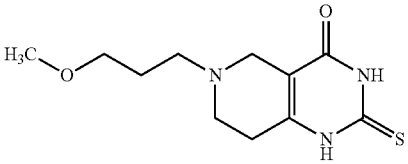 [SMILES: COCCCN1CCc2[nH]c(=S)[nH]c(=O)c2C1] | F1605-0391 | 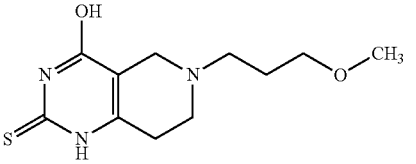 [SMILES: COCCCN1CCc2[nH]c(=S)nc(O)c2C1] | F1605-0391_4_1 (1 of 37) |
| Compound 64 | 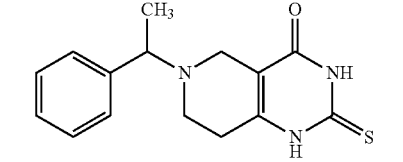 [SMILES: CC(c1ccccc1)N1CCc2[nH]c(=S)[nH]c(=O)c2C1] | F1607-0384 | 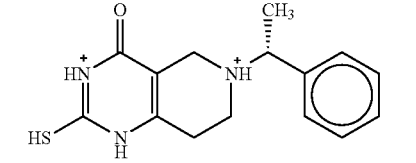 | F1607-0384_32_1 (1 of 66) |
| Compound 65 | 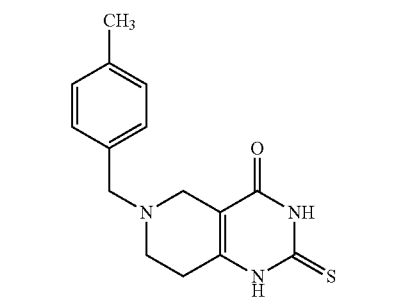 [SMILES: Cc1ccc(CN2CCc3[nH]c(=S)[nH]c(=O)c3C2)cc1] | F1607-0387 | 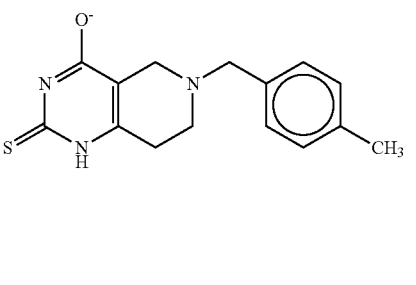 | F1607-0387_33_1 (1 of 33) |
| Compound 66 | 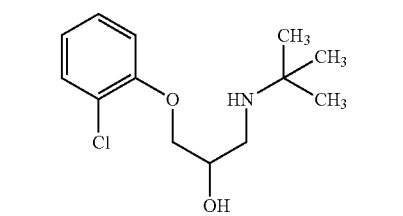 [SMILES: CC(C)(C)NCC(O)COc1ccccc1Cl] | F1630-0018 | 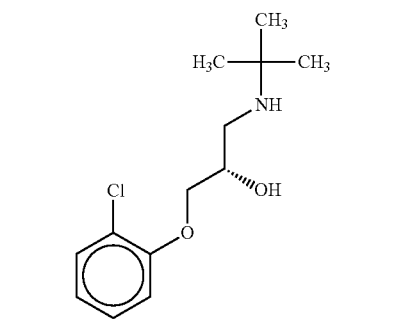 | F1630-0018_2 (1 of 4) |
| Compound 67 | 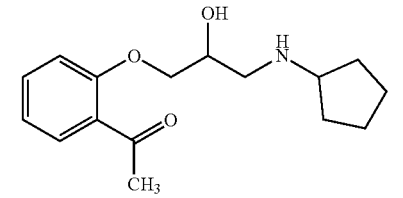 [SMILES: CC(=O)c1ccccc1OCC(O)CNC1CCCC1] | F1681-0025 | 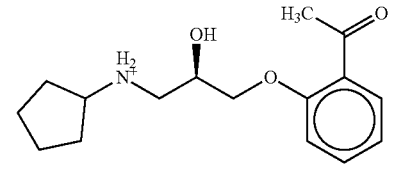 | F1681-0025_1_2 (1 of 4) |

TABLE 1-continued

| Compound x | Structure | No. | Tautomere/Stereoisomer | Reference of Variant |
|---|---|---|---|---|
| Compound 68 | 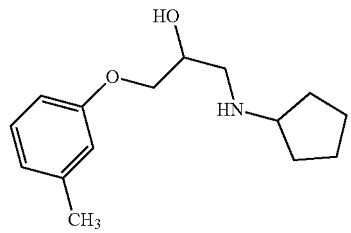 [SMILES: Cc1cccc(OCC(O)CNC2CCCC2)c1] | F1681-0068 | | F1681-0068_2 (1 of 4) |
| Compound 69 | 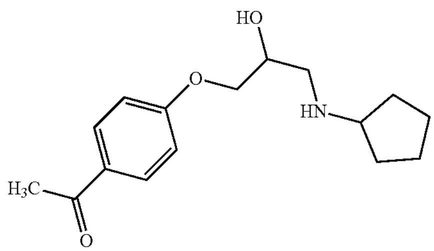 [SMILES: CC(=O)c1ccc(OCC(O)CNC2CCCC2)cc1] | F1681-0091 | | F1681-0091_1 (1 of 4) |
| Compound 70 | 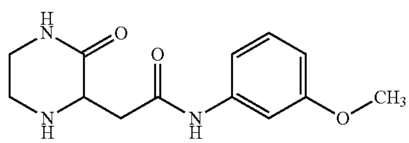 [SMILES: COc1cccc(NC(=O)CC2NCCNC2=O)c1] | F1709-0008 | | F1709-0008_1_1 (1 of 4) |
| Compound 71 | 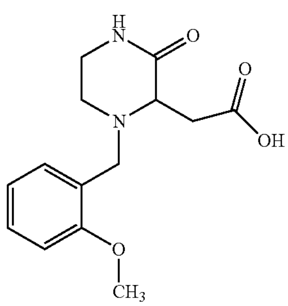 [SMILES: COc1ccccc1CN1CCNC(=O)C1CC(=O)O] | F1723-0297 | | F1723-0297_2_2 (1 of 8) |
| Compound 72 | 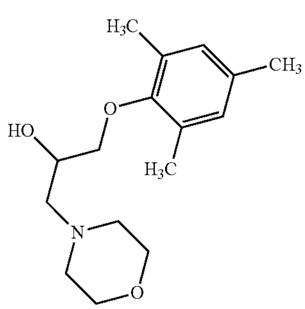 [SMILES: Cc1cc(C)c(OCC(O)CN2CCOCC2)c(C)c1] | F1725-0012 | | F1725-0012_1_1 (1 of 4) |

TABLE 1-continued

| Compound x | Structure | No. | Tautomere/Stereoisomer | Reference of Variant |
|---|---|---|---|---|
| Compound 73 | 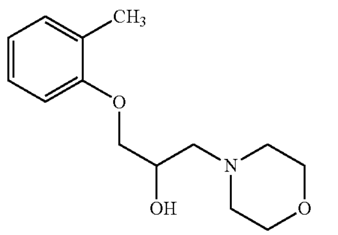 [SMILES: Cc1ccccc1OCC(O)CN1CCOCC1] | F1771-0001 | | F1771-0001_2 (1 of 4) |
| Compound 74 | 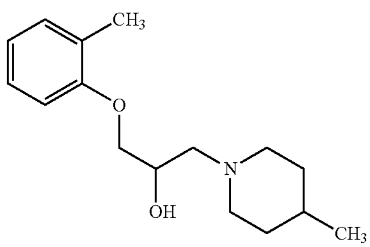 [SMILES: Cc1ccccc1OCC(O)CN1CCC(C)CC1] | F1771-0003 | | F1771-0003_1_2 (1 of 4) |
| Compound 75 | 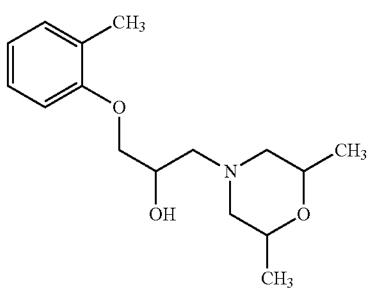 [SMILES: Cc1ccccc1OCC(O)CN1CC(C)OC(C)C1] | F1771-0007 | | F1771-0007_1_8 (1 of 16) |
| Compound 76 | 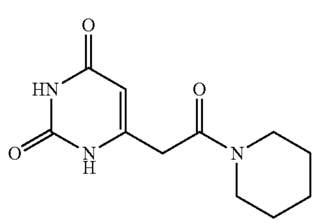 [SMILES: O=C(Cc1cc(=O)[nH]c(=O)[nH]1)N1CCCCC1] | F1811-0028 | | F1811-0028_57_1 (1 of 139) |
| Compound 77 | 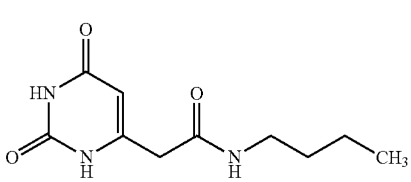 [SMILES: CCCCNC(=O)Cc1cc(=O)[nH]c(=O)[nH]1] | F1811-0068 | | F1811-0068_142_1 (1 of 211) |

TABLE 1-continued

| Compound x | Structure | No. | Tautomere/Stereoisomer | Reference of Variant |
|---|---|---|---|---|
| Compound 78 | 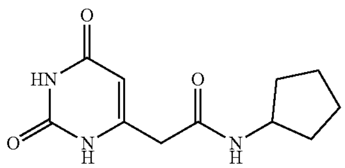 [SMILES: O=C(Cc1cc(=O)[nH]c(=O)[nH]1)NC1CCCC1] | F1811-0098 | | F1811-0098_148_1 (1 of 238) |
| Compound 79 | 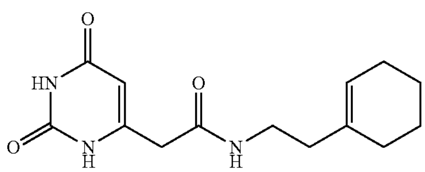 [SMILES: O=C(Cc1cc(=O)[nH]c(=O)[nH]1)NCCC1=CCCCC1] | F1811-0101 | | F1811-0101_142_1 (1 of 203) |
| Compound 80 | 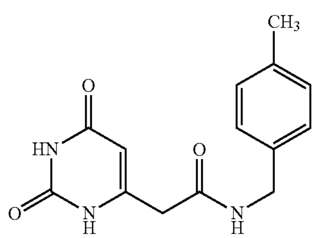 [SMILES: Cc1ccc(CNC(=O)Cc2cc(=O)[nH]c(=O)[nH]2)cc1] | F1811-0112 | | F1811-0112_137_1 (1 of 192) |
| Compound 81 | 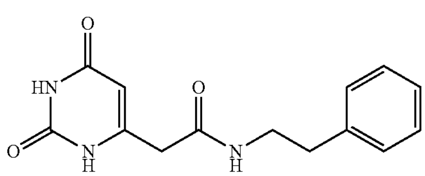 [SMILES: O=C(Cc1cc(=O)[nH]c(=O)[nH]1)NCCc1ccccc1] | F1811-0121 | | F1811-0121_142_1 (1 of 171) |
| Compound 82 | 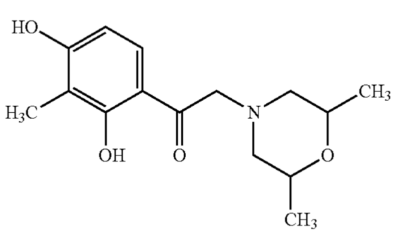 [SMILES: Cc1c(O)ccc(C(=O)CN2CC(C)OC(C)C2)c1O] | F1863-0017 | | F1863-0017_2 (1 of 28) |

TABLE 1-continued

| Compound x | Structure | No. | Tautomere/Stereoisomer | Reference of Variant |
|---|---|---|---|---|
| Compound 83 | 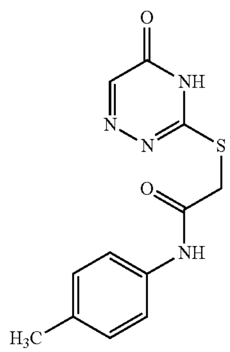 [SMILES: Cc1ccc(NC(=O)CSc2nncc(=O)[nH]2)cc1] | F1894-0028 | | F1894-0028_3_1 (1 of 6) |
| Compound 84 | 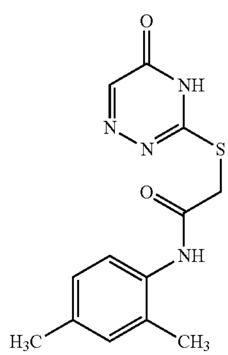 [SMILES: Cc1ccc(NC(=O)CSc2nncc(=O)[nH]2)c(C)c1] | F1894-0031 | | F1894-0031_3_1 (1 of 3) |
| Compound 85 | 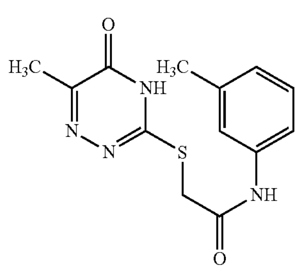 [SMILES: Cc1cccc(NC(=O)CSc2nnc(C)c(=O)[nH]2)c1] | F1894-0157 | | F1894-0157_3_1 (1 of 5) |
| Compound 86 | 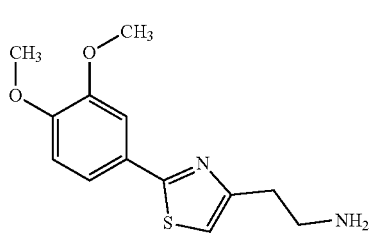 [SMILES: COc1ccc(-c2nc(CCN)cs2)cc1OC] | F1967-1078 | | F1967-1078_1 (1 of 4) |

TABLE 1-continued

| Compound x | Structure | No. | Tautomere/Stereoisomer | Reference of Variant |
|---|---|---|---|---|
| Compound 87 | 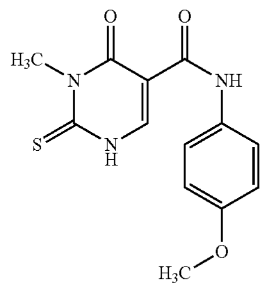 [SMILES: COc1ccc(NC(=O)c2c[nH]c(=S)n(C)c2=O)cc1] | F1967-1118 | | F1967-1118_22_1 (1 of 41) |
| Compound 88 | 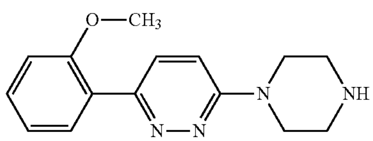 [SMILES: COc1ccccc1-c1ccc(N2CCNCC2)nn1] | F1967-1334 | | F1967-1334_1_1 (1 of 2) |
| Compound 89 | 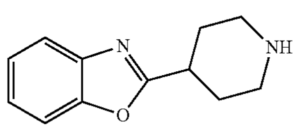 [SMILES: c1ccc2oc(C3CCNCC3)nc2c1] | F1984-0137 | | F1984-0137_3_1 (1 of 4) |
| Compound 90 | 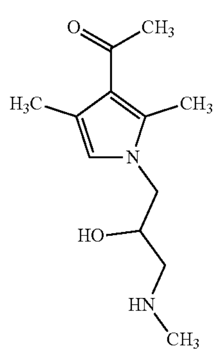 | F1986-0021 | | F1986-0021_1 (1 of 4) |

TABLE 1-continued

| Compound x | Structure | No. | Tautomere/Stereoisomer | Reference of Variant |
|---|---|---|---|---|
| Compound 91 | 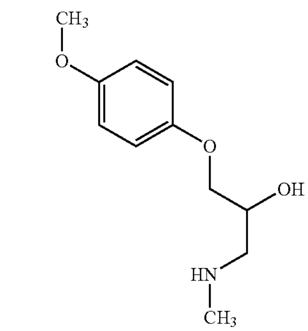 | F1986-0024 | | F1986-0024_1_1 (1 of 4) |
| Compound 92 | 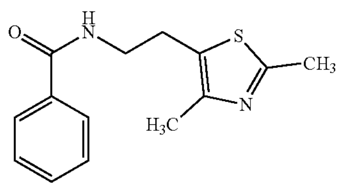 [SMILES: Cc1nc(C)c(CCNC(=O)c2ccccc2)s1] | F2011-0385 | | F2011-0385_1 (1 of 2) |
| Compound 93 | 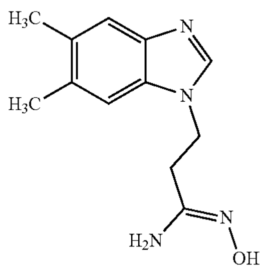 [SMILES: Cc1cc2ncn(CC/C(N)=N/O)c2cc1C] | F2101-0054 | | F2101-0054_8_1 (1 of 18) |
| Compound 94 | 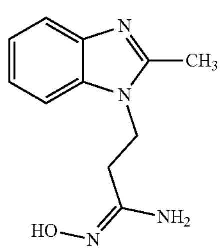 [SMILES: Cc1nc2ccccc2n1CC/C(N)=N\O] | F2101-0132 | | F2101-0132_7_1 (1 of 18) |
| Compound 95 | 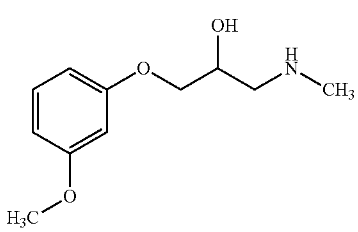 | F2137-0016 | | F2137-0016_1_1 (1 of 4) |

TABLE 1-continued

| Compound x | Structure | No. | Tautomere/Stereoisomer | Reference of Variant |
|---|---|---|---|---|
| Compound 96 | 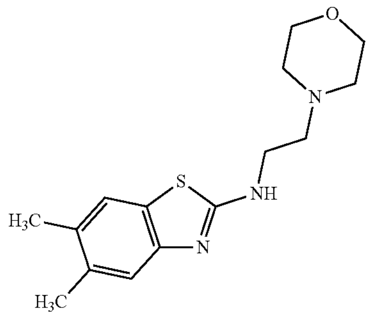 [SMILES: Cc1cc2nc(NCCN3CCOCC3)sc2cc1C] | F2145-0090 | | F2145-0090_3_1 (1 of 4) |
| Compound 97 | 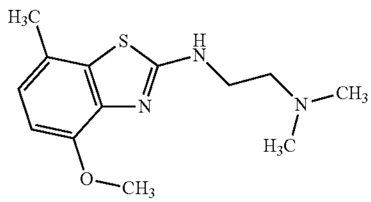 [SMILES: COc1ccc(C)c2sc(NCCN(C)C)nc12] | F2145-0296 | | F2145-0296_3_1 (1 of 4) |
| Compound 98 | 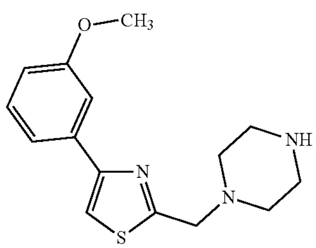 [SMILES: COc1cccc(-c2csc(CN3CCNCC3)n2)c1] | F2145-0373 | | F2145-0373_3_1 (1 of 7) |
| Compound 99 | 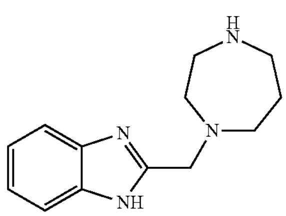 [SMILES: c1ccc2[nH]c(CN3CCCNCC3)nc2c1] | F2145-0423 | | F2145-0423_5_1 (1 of 7) |
| Compound 100 | 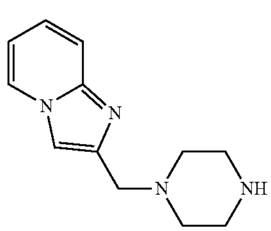 [SMILES: c1ccn2cc(CN3CCNCC3)nc2c1] | F2145-0424 | | F2145-0424_1_1 (1 of 7) |
| Compound 102 | 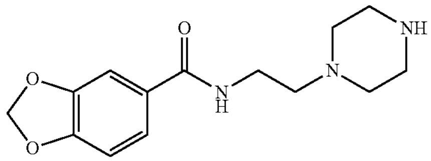 [SMILES: O=C(NCCN1CCNCC1)c1ccc2c(c1)OCO2] | F2145-0478 | | F2145-0478_2_1 (1 of 4) |

TABLE 1-continued

| Compound x | Structure | No. | Tautomere/Stereoisomer | Reference of Variant |
|---|---|---|---|---|
| Compound 103 | 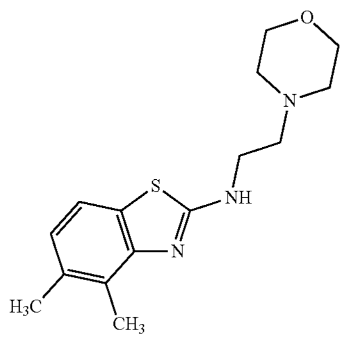 [SMILES: Cc1ccc2sc(NCCN3CCOCC3)nc2c1C] | F2146-0582 | | F2146-0582_3_1 (1 of 4) |
| Compound 104 | 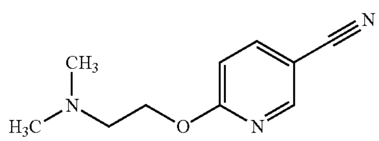 | F2147-0176 | | F2147-0176_1_1 (1 of 4) |
| Compound 105 | 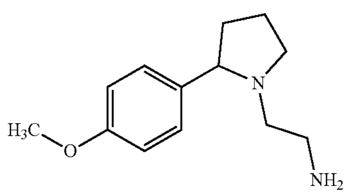 [SMILES: COc1ccc(C2CCCN2CCN)cc1] | F2147-0549 | | F2147-0549_3_2 (1 of 8) |
| Compound 106 | 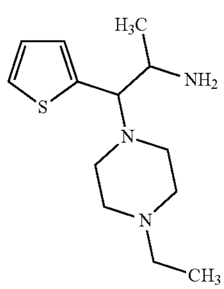 [SMILES: CCN1CCN(C(c2cccs2)C(C)N)CC1] | F2148-0005 | | F2148-0005_6_4 (1 of 28) |
| Compound 107 | 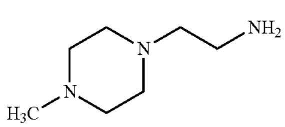 | F2148-0237 | | F2148-0237_2_1 (1 of 7) |
| Compound 108 | 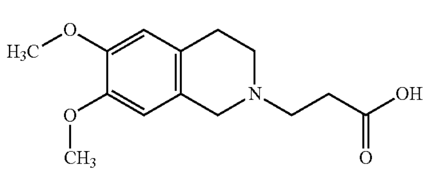 [SMILES: COc1cc2c(cc1OC)CN(CCC(=O)O)CC2] | F2150-0003 | | F2150-0003_3_1 (1 of 4) |

TABLE 1-continued

| Compound x | Structure | No. | Tautomere/Stereoisomer | Reference of Variant |
|---|---|---|---|---|
| Compound 109 | 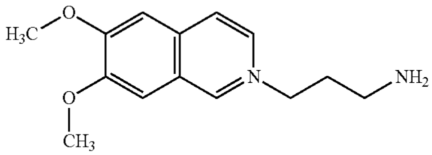 | F2150-0040 | | F2150-0040_3_1 (1 of 4) |
| Compound 110 | 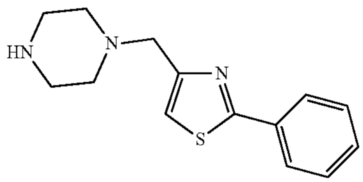 [SMILES: c1ccc(-c2nc(CN3CCNCC3)cs2)cc1] | F2158-0133 | | F2158-0133_1_1 (1 of 7) |
| Compound 111 | 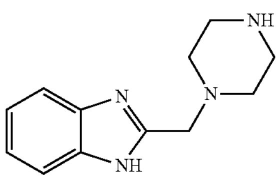 [SMILES: c1ccc2[nH]c(CN3CCNCC3)nc2c1] | F2158-0625 | | F2158-0625_1 (1 of 7) |
| Compound 112 | 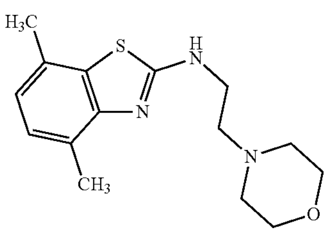 [SMILES: Cc1ccc(C)c2sc(NCCN3CCOCC3)nc12] | F2158-0833 | | F2158-0833_3_1 (1 of 4) |
| Compound 113 | 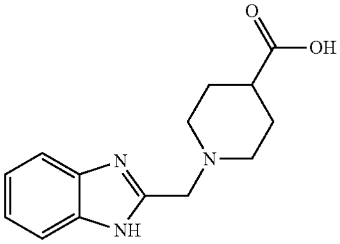 [SMILES: O=C(O)C1CCN(Cc2nc3ccccc3[nH]2)CC1] | F2158-1073 | | F2158-1073_4_1 (1 of 7) |

TABLE 1-continued

| Compound x | Structure | No. | Tautomere/Stereoisomer | Reference of Variant |
|---|---|---|---|---|
| Compound 114 | 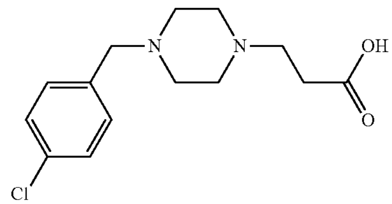 [SMILES: O=C(O)CCN1CCN(Cc2ccc(Cl)cc2)CC1] | F2164-0018 | | F2164-0018_5_1 (1 of 7) |
| Compound 115 | 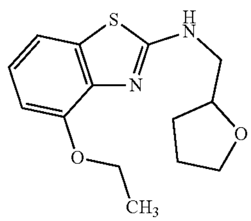 [SMILES: CCOc1cccc2sc(NCC3CCCO3)nc12] | F2182-0033 | | F2182-0033_1_2 (1 of 4) |
| Compound 116 | 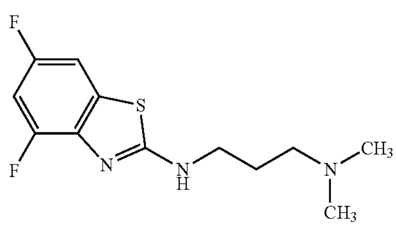 [SMILES: CN(C)CCCNc1nc2c(F)cc(F)cc2s1] | F2182-0073 | | F2182-0073_3_1 (1 of 4) |
| Compound 117 | 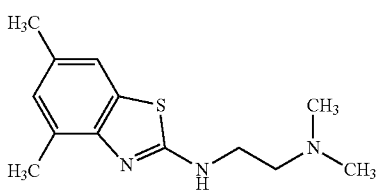 [SMILES: Cc1cc(C)c2nc(NCCN(C)C)sc2c1] | F2182-0075 | | F2182-0075_3_1 (1 of 4) |
| Compound 118 | 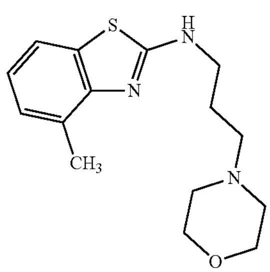 [SMILES: Cc1cccc2sc(NCCCN3CCOCC3)nc12] | F2182-0085 | | F2182-0085_1_1 (1 of 4) |
| Compound 119 | 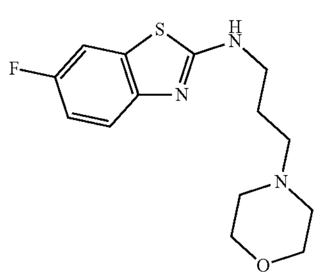 [SMILES: Fc1ccc2nc(NCCCN3CCOCC3)sc2c1] | F2182-0091 | | F2182-0091_1_1 (1 of 4) |

TABLE 1-continued

| Compound x | Structure | No. | Tautomere/Stereoisomer | Reference of Variant |
|---|---|---|---|---|
| Compound 120 | 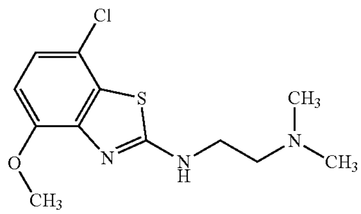 [SMILES: COc1ccc(Cl)c2sc(NCCN(C)C)nc12] | F2182-0097 | | F2182-0097_1_1 (1 of 4) |
| Compound 121 | 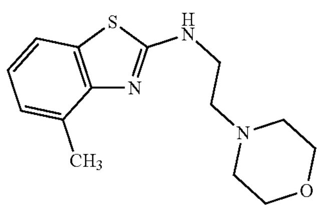 [SMILES: Cc1cccc2sc(NCCN3CCOCC3)nc12] | F2182-0103 | | F2182-0103_3_1 (1 of 4) |
| Compound 122 | 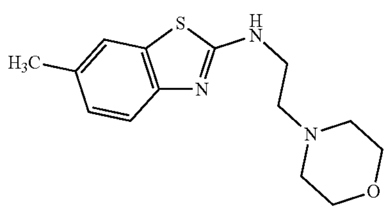 [SMILES: Cc1ccc2nc(NCCN3CCOCC3)sc2c1] | F2182-0106 | | F2182-0106_3_1 (1 of 4) |
| Compound 123 | 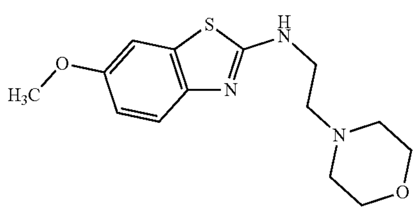 [SMILES: COc1ccc2nc(NCCN3CCOCC3)sc2c1] | F2182-0107 | | F2182-0107_1_1 (1 of 4) |
| Compound 124 | 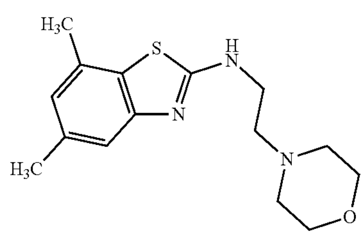 [SMILES: Cc1cc(C)c2sc(NCCN3CCOCC3)nc2c1] | F2182-0112 | | F2182-0112_1_1 (1 of 4) |
| Compound 125 | 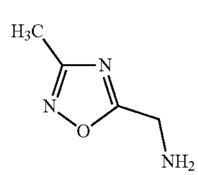 | F2185-0004 | | F2185-0004_3_1 (1 of 4) |

TABLE 1-continued

| Compound x | Structure | No. | Tautomere/Stereoisomer | Reference of Variant |
|---|---|---|---|---|
| Compound 126 | 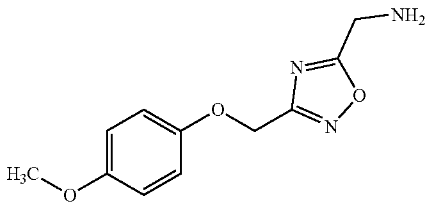 [SMILES: COc1ccc(OCc2noc(CN)n2)cc1] | F2185-0006 | | F2185-0006_1_1 (1 of 4) |
| Compound 127 | 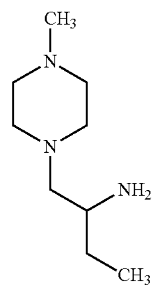 | F2185-0014 | | F2185-0014_3_2 (1 of 14) |
| Compound 128 | 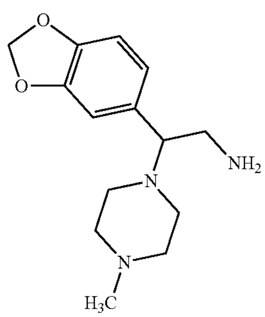 [SMILES: CN1CCN(C(CN)c2ccc3c(c2)OCO3)CC1] | F2189-0334 | | F2189-0334_5_2 (1 of 14) |
| Compound 129 | 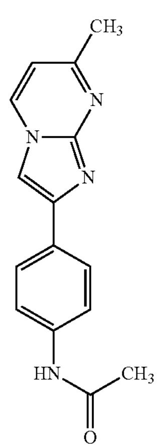 [SMILES: CC(=O)Nc1ccc(-c2cn3ccc(C)nc3n2)cc1] | F2206-0079 | | F2206-0079_2_1 (1 of 3) |

TABLE 1-continued

| Compound x | Structure | No. | Tautomere/Stereoisomer | Reference of Variant |
|---|---|---|---|---|
| Compound 130 | 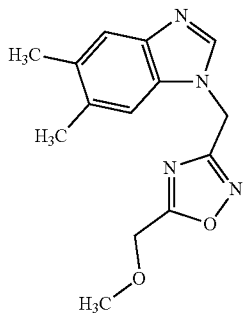 [SMILES: COCc1nc(Cn2cnc3cc(C)c(C)cc32)no1] | F2274-0585 | | F2274-0585_3_1 (1 of 4) |
| Compound 131 | 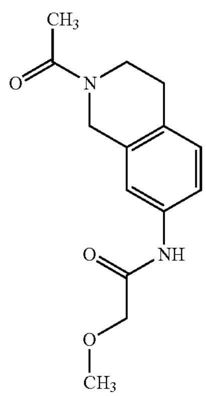 [SMILES: COCC(=O)Nc1ccc2c(c1)CN(C(C)=O)CC2] | F2416-0083 | | F2416-0083_1 (1 of 1) |
| Compound 132 | 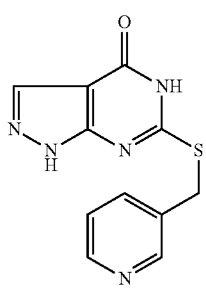 [SMILES: O=c1[nH]c(SCc2cccnc2)nc2[nH]ncc12] | F2503-0105 | | F2503-0105_22_1 (1 of 39) |
| Compound 133 | 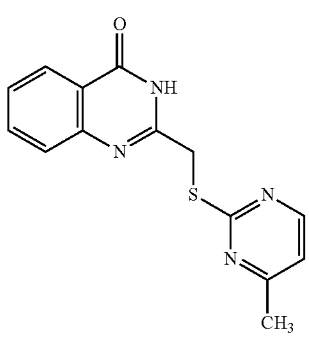 [SMILES: Cc1ccnc(SCc2nc3ccccc3c(=O)[nH]2)n1] | F2551-0031 | | F2551-0031_2_1 (1 of 18) |
| Compound 134 | 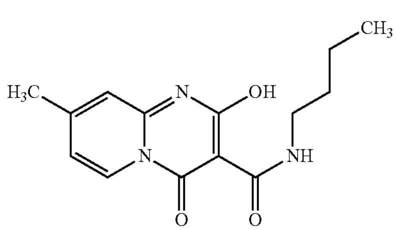 [SMILES: CCCCNC(=O)c1c(O)nc2cc(C)ccn2c1=O] | F2622-0072 | | F2622-0072_41_1 (1 of 129) |

TABLE 1-continued

| Compound x | Structure | No. | Tautomere/Stereoisomer | Reference of Variant |
|---|---|---|---|---|
| Compound 135 | 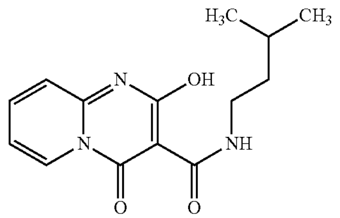 [SMILES: CC(C)CCNC(=O)c1c(O)nc2ccccn2c1=O] | F2622-0218 | | F2622-0218_20_1 (1 of 40) |
| Compound 136 | 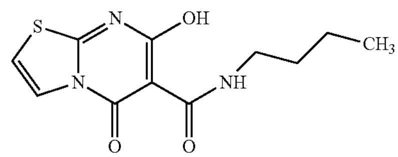 [SMILES: CCCCNC(=O)c1c(O)nc2sccn2c1=O] | F2624-0002 | | F2624-0002_7_1 (1 of 40) |
| Compound 137 | 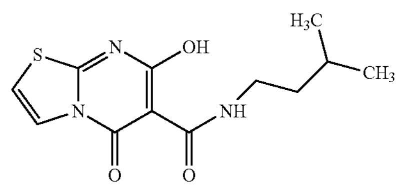 [SMILES: CC(C)CCNC(=O)c1c(O)nc2sccn2c1=O] | F2624-0008 | | F2624-0008_7_1 (1 of 40) |
| Compound 138 | 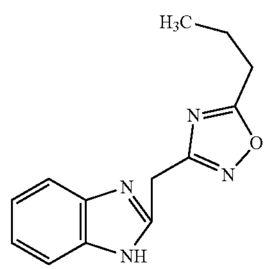 [SMILES: CCCc1nc(Cc2nc3ccccc3[nH]2)no1] | F2643-0132 | | F2643-0132_2_1 (1 of 4) |
| Compound 139 | 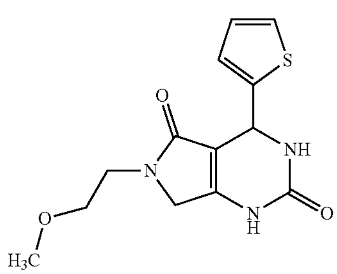 [SMILES: COCCN1CC2=C(C1=O)C(c1cccs1)NC(=O)N2] | F2711-1093 | | F2711-1093_10_1 (1 of 60) |
| Compound 140 | 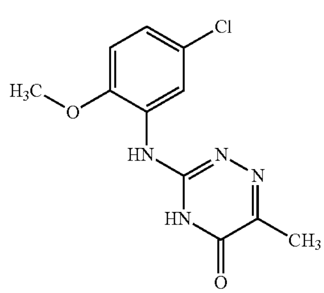 | F2713-0139 | | F2713-0139_4_1 (1 of 5) |

TABLE 1-continued

| Compound x | Structure | No. | Tautomere/Stereoisomer | Reference of Variant |
|---|---|---|---|---|
| Compound 141 | 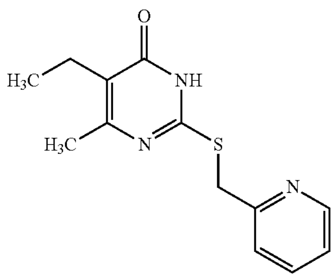 [SMILES: CCc1c(C)nc(SCc2ccccn2)[nH]c1=O] | F2716-0876 | | F2716-0876_15_1 (1 of 14) |
| Compound 142 | 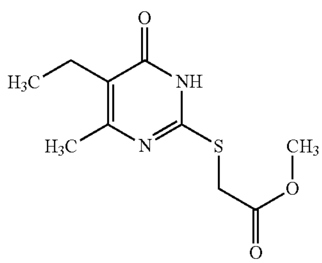 [SMILES: CCc1c(C)nc(SCC(=O)OC)[nH]c1=O] | F2716-0877 | | F2716-0877_6_1 (1 of 8) |
| Compound 143 | 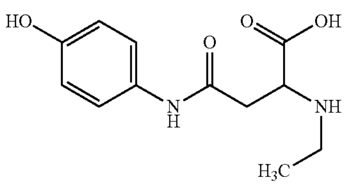 [SMILES: CCNC(CC(=O)Nc1ccc(O)cc1)C(=O)O] | F2721-0110 | | F2721-0110_6_2 (1 of 14) |
| Compound 144 | 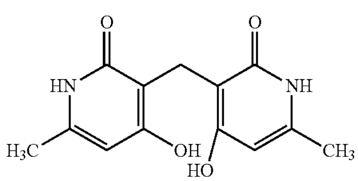 | F2811-0081 | | F2811-0081_150_4 (1 of 451) |
| Compound 145 | 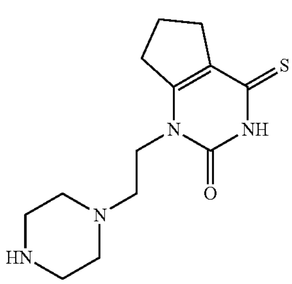 [SMILES: O=c1[nH]c(=S)c2c(n1CCN1CCNCC1)CCC2] | F2882-0062 | | F2882-0062_1_1 (1 of 21) |

TABLE 1-continued

| Compound x | Structure | No. | Tautomere/Stereoisomer | Reference of Variant |
|---|---|---|---|---|
| Compound 146 | 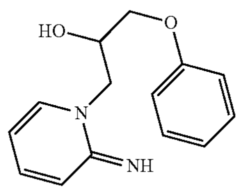 [SMILES: N=c1ccccn1CC(O)COc1ccccc1] | F3012-0022 | | F3012-0022_1_2 (1 of 4) |
| Compound 147 | 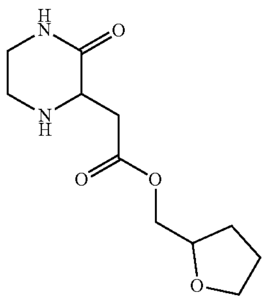 [SMILES: O=C(CC1NCCNC1=O)OCC1CCCO1] | F3034-0039 | | F3034-0039_1 (1 of 8) |
| Compound 148 | 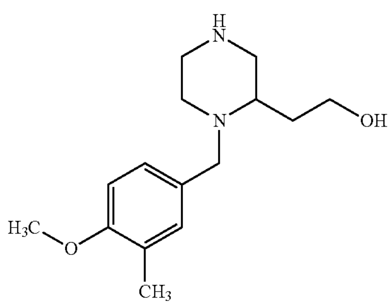 [SMILES: COc1ccc(CN2CCNCC2CCO)cc1C] | F3034-0286 | | F3034-0286_3_2 (1 of 4) |
| Compound 149 | 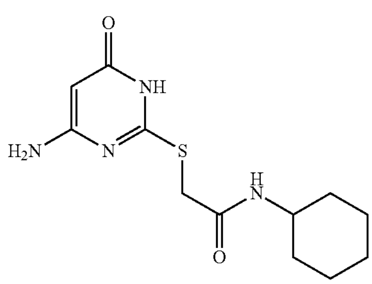 [SMILES: Nc1cc(=O)[nH]c(SCC(=O)NC2CCCCC2)n1] | F3045-0001 | | F3045-0001_11_1 (1 of 14) |
| Compound 150 | 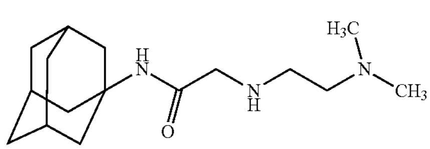 [SMILES: CN(C)CCNCC(=O)NC12CC3CC(CC(C3)C1)C2] | F3084-0058 | | F3084-0058_2_1 (1 of 4) |

TABLE 1-continued

| Compound x | Structure | Compound No. | Tautomere/Stereoisomer | Reference of Variant |
|---|---|---|---|---|
| Compound 151 | 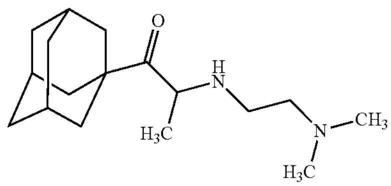 [SMILES: CC(NCCN(C)C)C(=O)C12CC3CC(CC(C3)C1)C2] | F3084-0157 | | F3084-0157_2_2 (1 of 8) |
| Compound 152 | 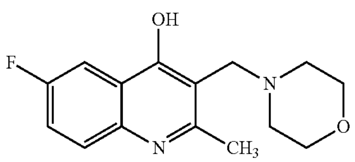 [SMILES: Cc1nc2ccc(F)cc2c(O)c1CN1CCOCC1] | F3099-0269 | | F3099-0269_1_1 (1 of 8) |
| Compound 153 | 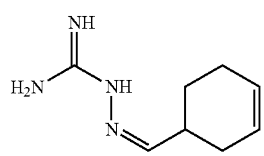 [SMILES: N=C(N)N/N=C\C1CC=CCC1] | F3099-3404 | | F3099-3404_29_2 (1 of 120) |
| Compound 154 | 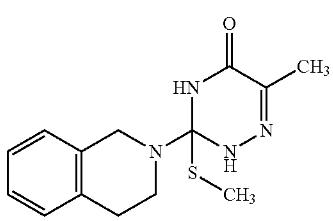 [SMILES: CSC1(N2CCc3ccccc3C2)NN=C(C)C(=O)N1] | F3099-3503 | | F3099-3503_1_2 (1 of 24) |
| Compound 155 | 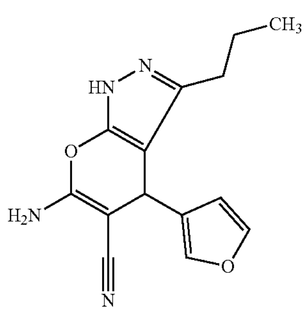 [SMILES: CCCc1n[nH]c2c1C(c1ccoc1)C(C#N)=C(N)O2] | F3129-0147 | | F3129-0147_6_3 (1 of 24) |

TABLE 1-continued

| Compound x | Structure | No. | Tautomere/Stereoisomer | Reference of Variant |
|---|---|---|---|---|
| Compound 156 | 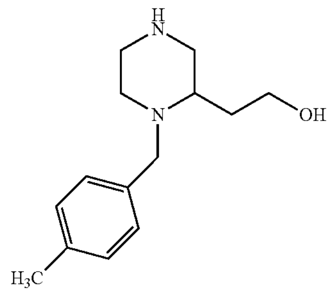 [SMILES: Cc1ccc(CN2CCNCC2CCO)cc1] | F3146-0231 | | F3146-0231_2_1 (1 of 8) |
| Compound 157 | 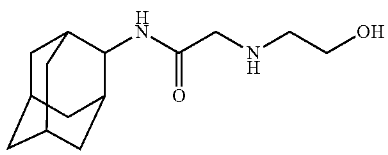 [SMILES: O=C(CNCCO)NC1C2CC3CC(C2)CC1C3] | F3154-0012 | | F3154-0012_1 (1 of 2) |
| Compound 158 | 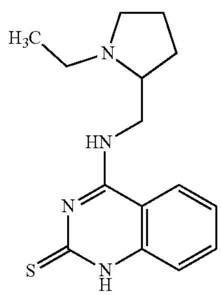 [SMILES: CCN1CCCC1CNc1nc(=S)[nH]c2ccccc12] | F3168-1703 | | F3168-1703_19_2 (1 of 46) |
| Compound 159 | 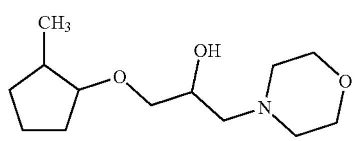 [SMILES: CC1CCCC1OCC(O)CN1CCOCC1] | F3200-0073 | | F3200-0073_1_1 (1 of 16) |
| Compound 160 | 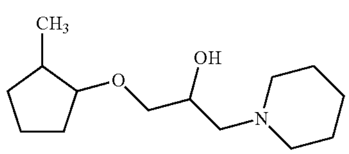 [SMILES: CC1CCCC1OCC(O)CN1CCCCC1] | F3200-0074 | | F3200-0074_1_1 (1 of 16) |
| Compound 161 | 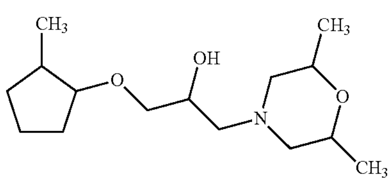 [SMILES: CC1CN(CC(O)COC2CCCC2C)CC(C)O1] | F3200-0076 | | F3200-0076_1_17 (1 of 53) |
| Compound 162 | 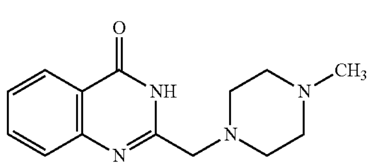 [SMILES: CN1CCN(Cc2nc3ccccc3c(=O)[nH]2)CC1] | F3219-0003 | | F3219-0003_23_1 (1 of 27) |

TABLE 1-continued

| Compound x | Structure | No. | Tautomere/Stereoisomer | Reference of Variant |
|---|---|---|---|---|
| Compound 163 | 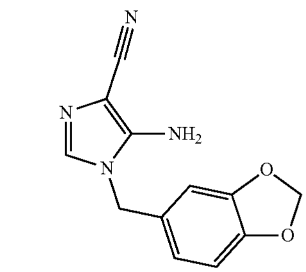 [SMILES: N#Cc1ncn(Cc2ccc3c(c2)OCO3)c1N] | F3225-8622 | | F3225-8622_3_1 (1 of 4) |
| Compound 164 | 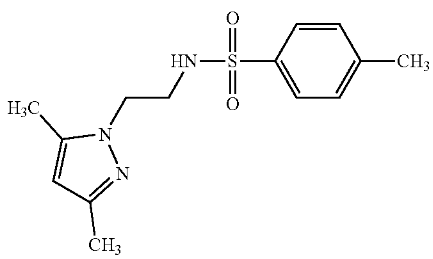 | F3230-0054 | | F3230-0054_1 (1 of 1) |
| Compound 165 | 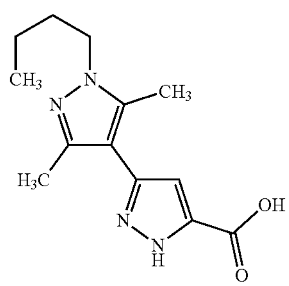 [SMILES: CCCCn1nc(C)c(-c2cc(C(=O)O)[nH]n2)c1C] | F3250-0673 | | F3250-0673_1 (1 of 4) |
| Compound 166 | 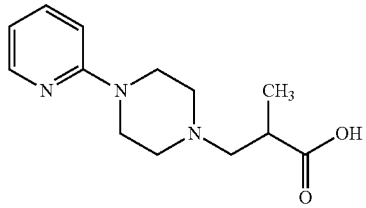 [SMILES: CC(CN1CCN(c2ccccn2)CC1)C(=O)O] | F3250-0686 | | F3250-0686_2_2 (1 of 14) |

TABLE 1-continued

| Compound x | Structure | No. | Tautomere/Stereoisomer | Reference of Variant |
|---|---|---|---|---|
| Compound 167 | 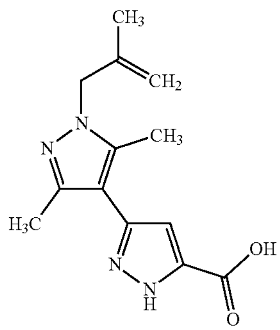 [SMILES: C=C(C)Cn1nc(C)c(-c2cc(C(=O)O)[nH]n2)c1C] | F3250-0689 | | F3250-0689_1 (1 of 4) |
| Compound 168 | 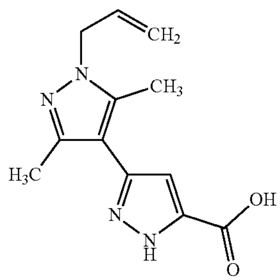 [SMILES: C=CCn1nc(C)c(-c2cc(C(=O)O)[nH]n2)c1C] | F3250-0696 | | F3250-0696_1 (1 of 4) |
| Compound 169 | 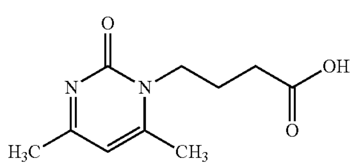 | F3250-0733 | | F3250-0733_1_1 (1 of 4) |
| Compound 170 | 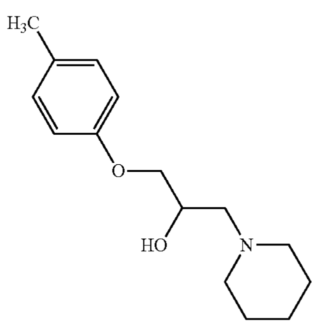 [SMILES: Cc1ccc(OCC(O)CN2CCCCC2)cc1] | F3254-0053 | | F3254-0053_1_1 (1 of 4) |
| Compound 171 | 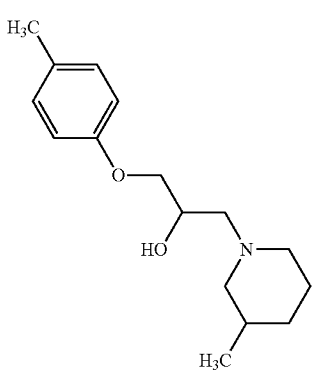 [SMILES: Cc1ccc(OCC(O)CN2CCCC(C)C2)cc1] | F3254-0054 | | F3254-0054_3 (1 of 8) |

TABLE 1-continued

| Compound x | Structure | No. | Tautomere/Stereoisomer | Reference of Variant |
|---|---|---|---|---|
| Compound 172 | 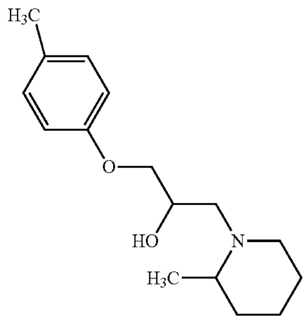 [SMILES: Cc1ccc(OCC(O)CN2CCCCC2C)cc1] | F3254-0055 | | F3254-0055_1_3 (1 of 8) |
| Compound 173 | 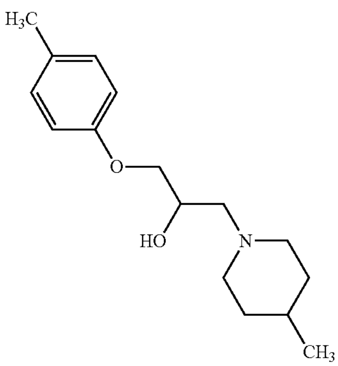 [SMILES: Cc1ccc(OCC(O)CN2CCC(C)CC2)cc1] | F3254-0056 | | F3254-0056_1 (1 of 4) |
| Compound 174 | 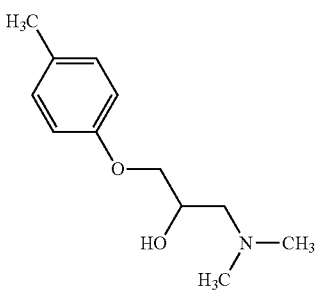 | F3254-0059 | | F3254-0059_1_1 (1 of 4) |
| Compound 175 | 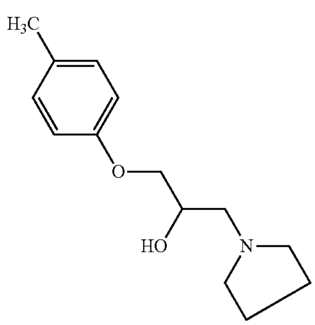 [SMILES: Cc1ccc(OCC(O)CN2CCCC2)cc1] | F3254-0063 | | F3254-0063_1 (1 of 4) |

TABLE 1-continued

| Compound x | Structure | No. | Tautomere/Stereoisomer | Reference of Variant |
|---|---|---|---|---|
| Compound 176 | 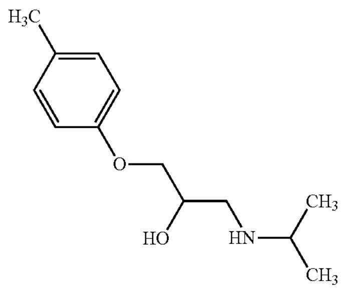 [SMILES: Cc1ccc(OCC(O)CNC(C)C)cc1] | F3254-0064 | | F3254-0064_1 (1 of 4) |
| Compound 177 | 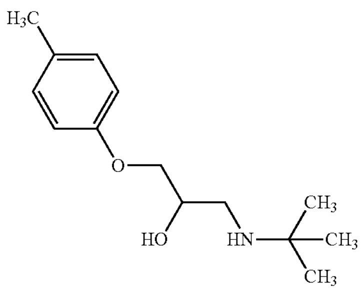 [SMILES: Cc1ccc(OCC(O)CNC(C)(C)C)cc1] | F3254-0065 | | F3254-0065_1_1 (1 of 4) |
| Compound 178 | 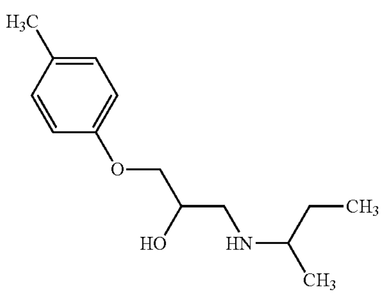 [SMILES: CCC(C)NCC(O)COc1ccc(C)cc1] | F3254-0073 | | F3254-0073_1_1 (1 of 8) |
| Compound 179 | 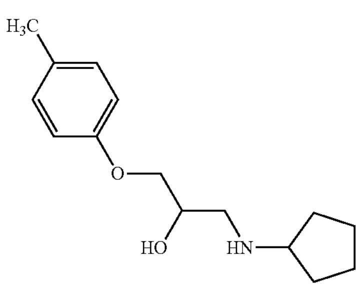 [SMILES: Cc1ccc(OCC(O)CNC2CCCC2)cc1] | F3254-0075 | | F3254-0075_1 (1 of 4) |

TABLE 1-continued

| Compound x | Structure | No. | Tautomere/Stereoisomer | Reference of Variant |
|---|---|---|---|---|
| Compound 180 | 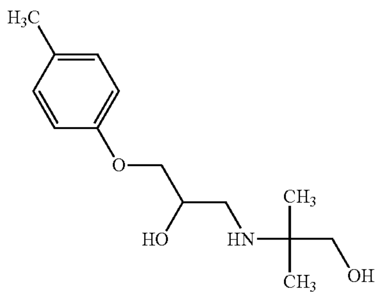 [SMILES: Cc1ccc(OCC(O)CNC(C)(C)CO)cc1] | F3254-0098 | | F3254-0098_1_2 (1 of 4) |
| Compound 181 | 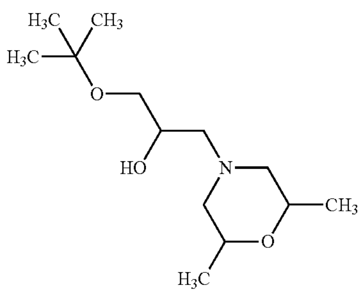 [SMILES: CC1CN(CC(O)COC(C)(C)C)CC(C)O1] | F3254-0105 | | F3254-0105_1_6 (1 of 16) |
| Compound 182 | 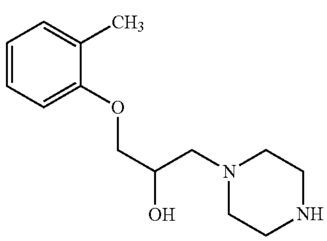 [SMILES: Cc1ccccc1OCC(O)CN1CCNCC1] | F3255-0157 | | F3255-0157_1_1 (1 of 8) |
| Compound 183 | 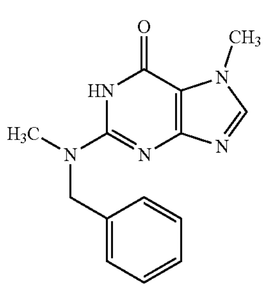 [SMILES: CN(Cc1ccccc1)c1nc2ncn(C)c2c(=O)[nH]1] | F3260-0881 | | F3260-0881_7_1 (1 of 13) |
| Compound 184 | 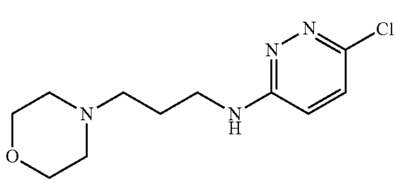 [SMILES: Clc1ccc(NCCCN2CCOCC2)nn1] | F3266-0086 | | F3266-0086_1_1 (1 of 2) |

TABLE 1-continued

| Compound x | Structure | No. | Tautomere/Stereoisomer | Reference of Variant |
|---|---|---|---|---|
| Compound 185 | 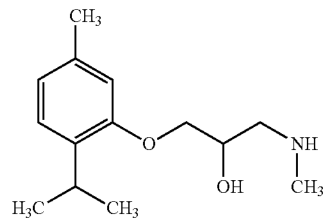 [SMILES: CNCC(O)COc1cc(C)ccc1C(C)C] | F3276-0018 | | F3276-0018_2 (1 of 4) |
| Compound 186 | 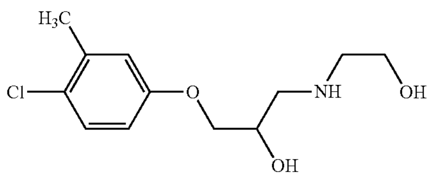 [SMILES: Cc1cc(OCC(O)CNCCO)ccc1Cl] | F3276-0031 | | F3276-0031_2 (1 of 4) |
| Compound 187 | 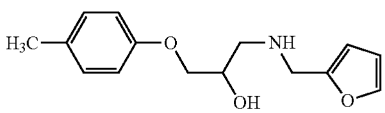 [SMILES: Cc1ccc(OCC(O)CNCc2ccco2)cc1] | F3276-0044 | | F3276-0044_2 (1 of 4) |
| Compound 188 | 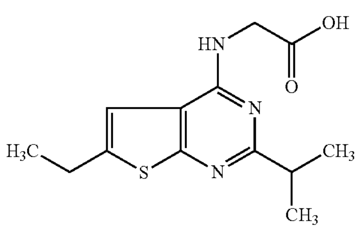 [SMILES: CCc1cc2c(NCC(=O)O)nc(C(C)C)nc2s1] | F3277-0798 | | F3277-0798_1_1 (1 of 2) |
| Compound 189 | 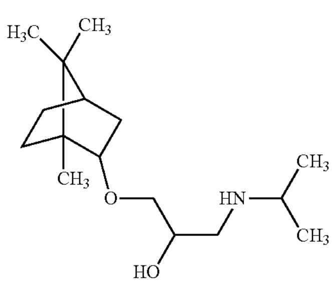 [SMILES: CC(C)NCC(O)COC1CC2CCC1(C)C2(C)C] | F3278-0013 | | F3278-0013_4 (1 of 8) |
| Compound 190 | 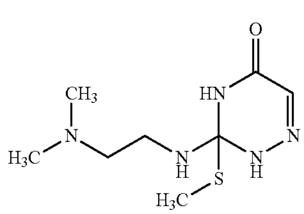 | F3284-7619 | | F3284-7619_2 (1 of 20) |

TABLE 1-continued

| Compound x | Structure | No. | Tautomere/Stereoisomer | Reference of Variant |
|---|---|---|---|---|
| Compound 191 | 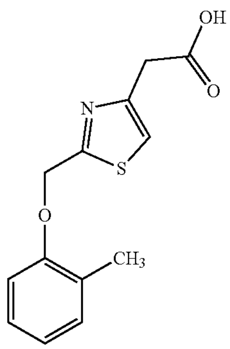 [SMILES: Cc1ccccc1OCc1nc(CC(=O)O)cs1] | F3284-7869 | | F3284-7869_1_1 (1 of 2) |
| Compound 192 | 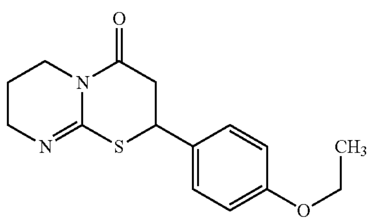 [SMILES: CCOc1ccc(C2CC(=O)N3CCCN=C3S2)cc1] | F3301-0129 | | F3301-0129_1_2 (1 of 4) |
| Compound 193 | 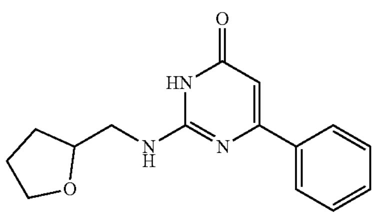 [SMILES: O=c1cc(-c2ccccc2)nc(NCC2CCCO2)[nH]1] | F3308-0605 | | F3308-0605_7_2 (1 of 16) |
| Compound 194 | 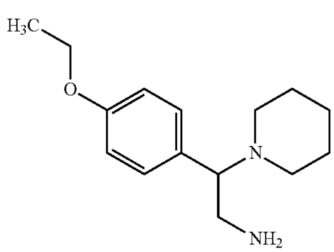 [SMILES: CCOc1ccc(C(CN)N2CCCCC2)cc1] | F3308-1206 | | F3308-1206_1 (1 of 8) |
| Compound 195 | 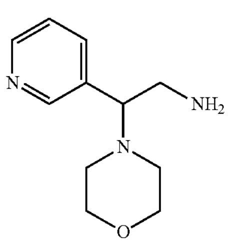 [SMILES: NCC(c1cccnc1)N1CCOCC1] | F3308-2774 | | F3308-2774_5_1 (1 of 14) |

TABLE 1-continued

| Compound x | Structure | No. | Tautomere/Stereoisomer | Reference of Variant |
|---|---|---|---|---|
| Compound 196 | 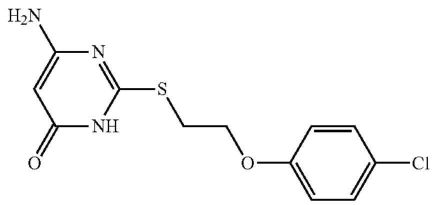 [SMILES: Nc1cc(=O)[nH]c(SCCOc2ccc(Cl)cc2)n1] | F3308-3248 | | F3308-3248_6_1 (1 of 12) |
| Compound 197 | 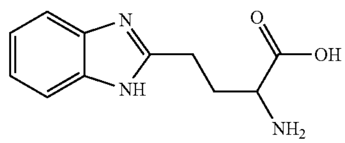 [SMILES: NC(CCc1nc2ccccc2[nH]1)C(=O)O] | F3308-3604 | | F3308-3604_3_1 (1 of 14) |
| Compound 198 | 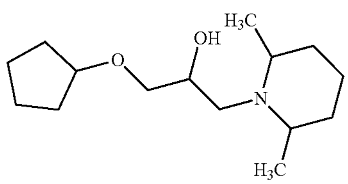 [SMILES: CC1CCCC(C)N1CC(O)COC1CCCC1] | F3314-0051 | | F3314-0051_1 (1 of 16) |
| Compound 199 | 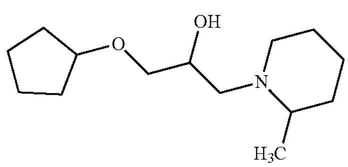 [SMILES: CC1CCCCN1CC(O)COC1CCCC1] | F3314-0053 | | F3314-0053_1_3 (1 of 8) |
| Compound 200 | 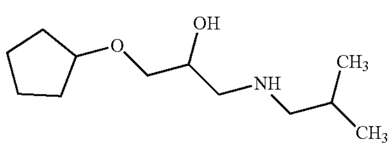 | F3314-0059 | | F3314-0059_2 (1 of 4) |
| Compound 201 | 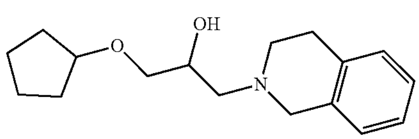 [SMILES: OC(COC1CCCC1)CN1CCc2ccccc2C1] | F3314-0071 | | F3314-0071_2 (1 of 4) |
| Compound 202 | 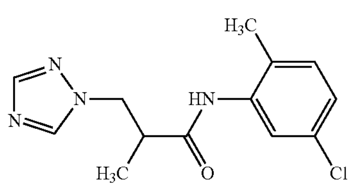 [SMILES: Cc1ccc(Cl)cc1NC(=O)C(C)Cn1cncn1] | F3316-0057 | | F3316-0057_1_2 (1 of 4) |
| Compound 203 | 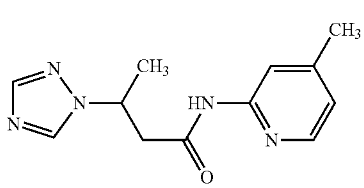 [SMILES: Cc1ccnc(NC(=O)CC(C)n2cncn2)c1] | F3316-0139 | | F3316-0139_3_2 (1 of 8) |

TABLE 1-continued

| Compound x | Structure | No. | Tautomere/Stereoisomer | Reference of Variant |
|---|---|---|---|---|
| Compound 204 | 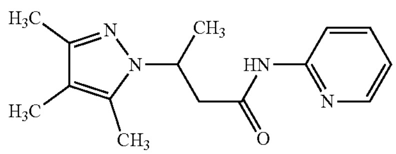 [SMILES: Cc1nn(C(C)CC(=O)Nc2ccccn2)c(C)c1C] | F3316-0145 | | F3316-0145_1_2 (1 of 4) |
| Compound 205 | 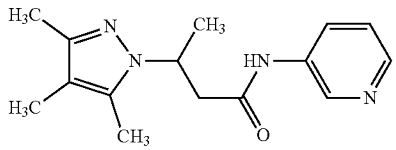 [SMILES: Cc1nn(C(C)CC(=O)Nc2cccnc2)c(C)c1C] | F3316-0146 | | F3316-0146_1_2 (1 of 4) |
| Compound 206 | 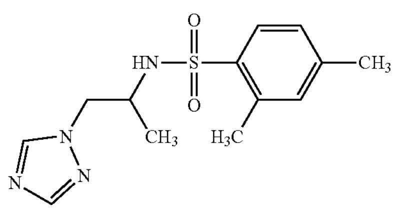 [SMILES: Cc1ccc(S(=O)(=O)NC(C)Cn2cncn2)c(C)c1] | F3316-0166 | | F3316-0166_1_1 (1 of 4) |
| Compound 207 | 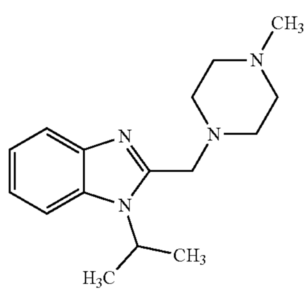 [SMILES: CC(C)n1c(CN2CCN(C)CC2)nc2ccccc21] | F3320-0301 | | F3320-0301_5_1 (1 of 7) |
| Compound 208 | 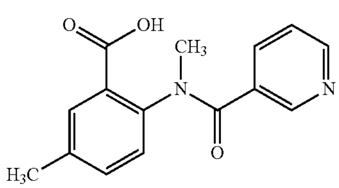 [SMILES: Cc1ccc(N(C)C(=O)c2cccnc2)c(C(=O)O)c1] | F3331-0647 | | F3331-0647_1_1 (1 of 4) |

TABLE 1-continued

| Compound x | Structure | Compound No. | Tautomere/Stereoisomer | Reference of Variant |
|---|---|---|---|---|
| Compound 209 | 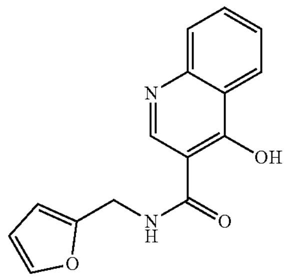 [SMILES: O=C(NCc1ccco1)c1cnc2ccccc2c1O] | F3350-0739 | | F3350-0739_1_1 (1 of 4) |
| Compound 210 | 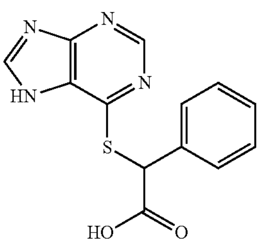 [SMILES: O=C(O)C(Sc1ncnc2nc[nH]c12)c1ccccc1] | F3358-0351 | | F3358-0351_18_2 (1 of 26) |
| Compound 211 | 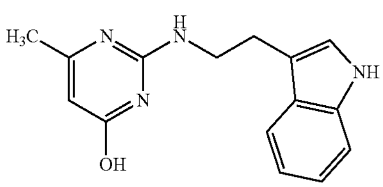 [SMILES: Cc1cc(O)nc(NCCc2c[nH]c3ccccc23)n1] | F3358-0389 | | F3358-0389_1_1 (1 of 8) |
| Compound 212 | 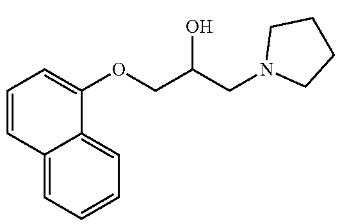 [SMILES: OC(COc1cccc2ccccc12)CN1CCCC1] | F3368-0119 | | F3368-0119_1_1 (1 of 4) |
| Compound 213 | 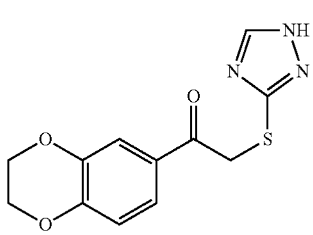 [SMILES: O=C(CSc1nc[nH]n1)c1ccc2c(c1)OCCO2] | F3394-1172 | | F3394-1172_1_1 (1 of 5) |

TABLE 1-continued

| Compound x | Structure | No. | Tautomere/Stereoisomer | Reference of Variant |
|---|---|---|---|---|
| Compound 214 | 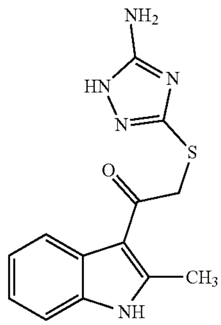 [SMILES: Cc1[nH]c2ccccc2c1C(=O)CSc1n[nH]c(N)n1] | F3394-1274 | | F3394-1274_4_1 (1 of 5) |
| Compound 215 | 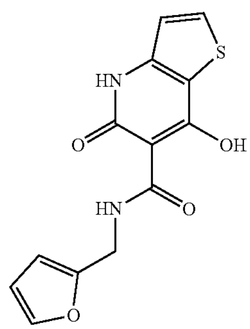 [SMILES: O=C(NCc1ccco1)c1c(O)c2sccc2[nH]c1=O] | F3406-8965 | | F3406-8965_39_2 (1 of 158) |
| Compound 216 | 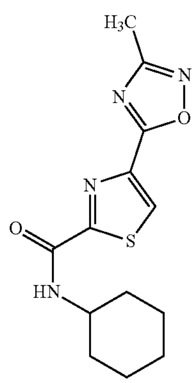 [SMILES: Cc1noc(-c2csc(C(=O)NC3CCCCC3)n2)n1] | F3407-5137 | | F3407-5137_3_1 (1 of 3) |
| Compound 217 | 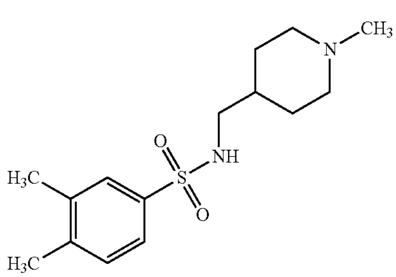 | F5017-0030 | | F5017-0030_1 (1 of 2) |

TABLE 1-continued

| Compound x | Structure | No. | Tautomere/Stereoisomer | Reference of Variant |
|---|---|---|---|---|
| Compound 218 | 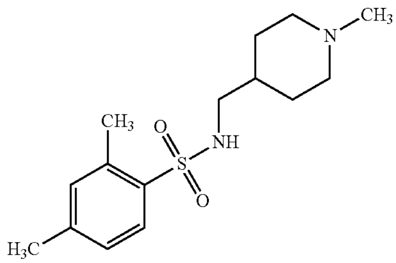 | F5017-0031 | | F5017-0031_1_1 (1 of 2) |
| Compound 219 | 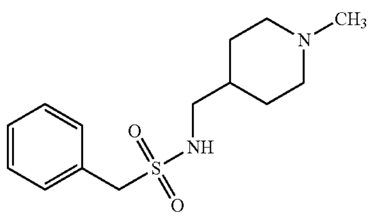 [SMILES: CN1CCC(CNS(=O)(=O)Cc2ccccc2)CC1] | F5017-0074 | | F5017-0074_1 (1 of 2) |
| Compound 220 | 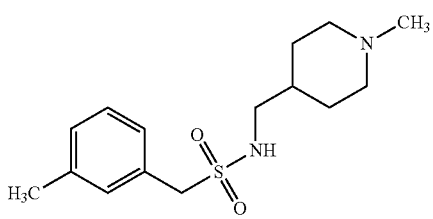 | F5017-0076 | | F5017-0076_1_1 (1 of 2) |
| Compound 221 | 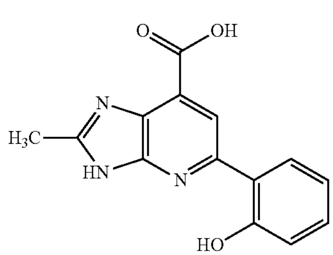 [SMILES: Cc1nc2c(C(=O)O)cc(-c3ccccc3O)nc2[nH]1] | F5080-0092 | | F5080-0092_14_1 (1 of 4) |

TABLE 1-continued

| Compound x | Structure | No. | Tautomere/Stereoisomer | Reference of Variant |
|---|---|---|---|---|
| Compound 222 | 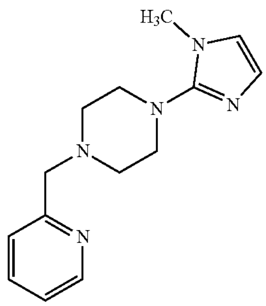 [SMILES: Cn1ccnc1N1CCN(Cc2ccccn2)CC1] | F5096-0076 | | F5096-0076_3_1 (1 of 7) |
| Compound 223 | 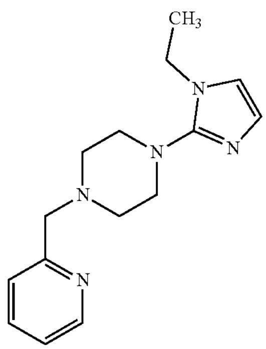 [SMILES: CCn1ccnc1N1CCN(Cc2ccccn2)CC1] | F5096-0179 | | F5096-0179_3_1 (1 of 7) |
| Compound 224 | 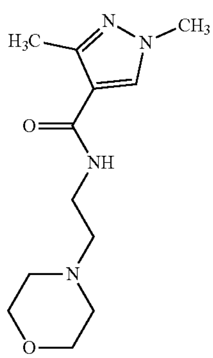 [SMILES: Cc1nn(C)cc1C(=O)NCCN1CCOCC1] | F5302-0092 | | F5302-0092_1_1 (1 of 2) |
| Compound 225 | 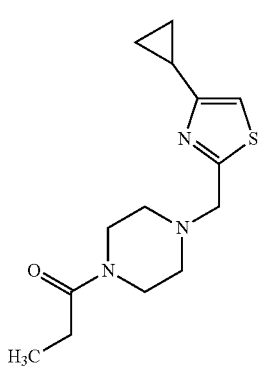 [SMILES: CCC(=O)N1CCN(Cc2nc(C3CC3)cs2)CC1] | F5461-1122 | | F5461-1122_1_1 (1 of 4) |

TABLE 1-continued

| Compound x | Structure | No. | Tautomere/Stereoisomer | Reference of Variant |
|---|---|---|---|---|
| Compound 226 | 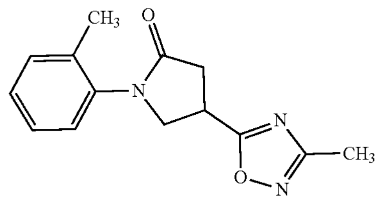 [SMILES: Cc1noc(C2CC(=O)N(c3ccccc3C)C2)n1] | F5668-0082 | | F5668-0082_1 (1 of 4) |
| Compound 227 | 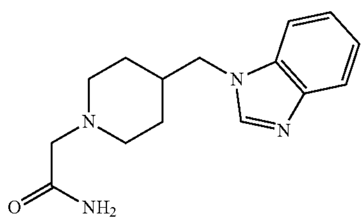 [SMILES: NC(=O)CN1CCC(Cn2cnc3ccccc32)CC1] | F5754-0084 | | F5754-0084_2_1 (1 of 4) |
| Compound 228 | 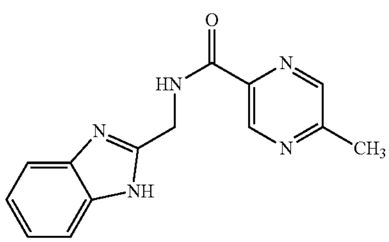 [SMILES: Cc1cnc(C(=O)NCc2nc3ccccc3[nH]2)cn1] | F5791-2428 | | F5791-2428_5_1 (1 of 6) |
| Compound 229 | 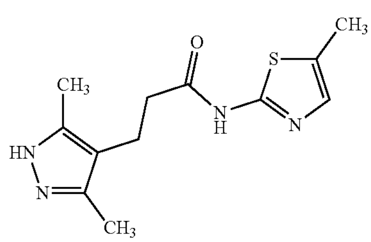 [SMILES: Cc1cnc(NC(=O)CCc2c(C)n[nH]c2C)s1] | F5806-0308 | | F5806-0308_1_1 (1 of 2) |
| Compound 230 | 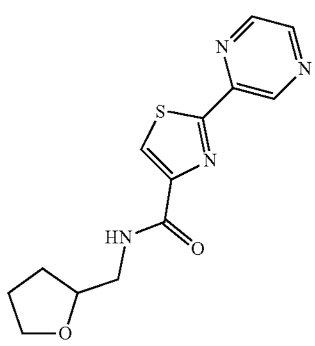 [SMILES: O=C(NCC1CCCO1)c1csc(-c2cnccn2)n1] | F5828-0220 | | F5828-0220_3_2 (1 of 14) |

TABLE 1-continued

| Compound x | Structure | Compound No. | Tautomere/Stereoisomer | Reference of Variant |
|---|---|---|---|---|
| Compound 231 | 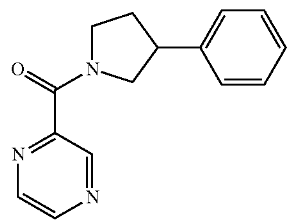 [SMILES: O=C(c1cnccn1)N1CCC(c2ccccc2)C1] | F5831-3069 | | F5831-3069_2_2 (1 of 8) |
| Compound 232 | 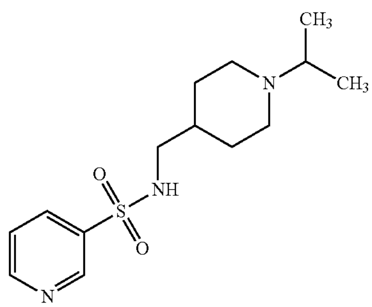 [SMILES: CC(C)N1CCC(CNS(=O)(=O)c2cccnc2)CC1] | F5831-6204 | | F5831-6204_1_1 (1 of 4) |
| Compound 233 | 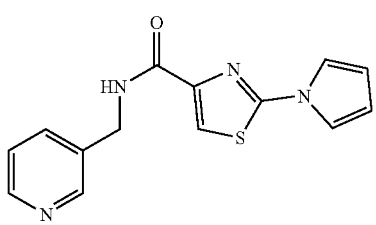 [SMILES: O=C(NCc1cccnc1)c1csc(-n2cccc2)n1] | F5856-0133 | | F5856-0133_3_1 (1 of 2) |
| Compound 234 | 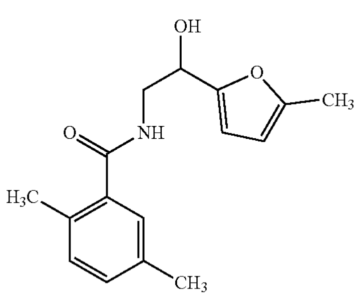 | F5857-0026 | | F5857-0026_1 (1 of 2) |

TABLE 1-continued

| Compound x | Structure | No. | Tautomere/Stereoisomer | Reference of Variant |
|---|---|---|---|---|
| Compound 235 | 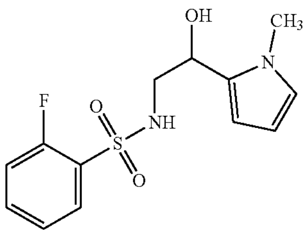 [SMILES: Cn1cccc1C(O)CNS(=O)(=O)c1ccccc1F] | F5857-0927 | | F5857-0927_1 (1 of 2) |
| Compound 236 | 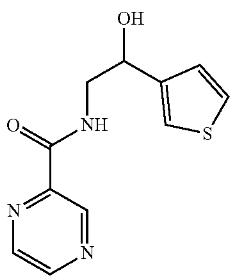 [SMILES: O=C(NCC(O)c1ccsc1)c1cnccn1] | F5857-1145 | | F5857-1145_1_1 (1 of 8) |
| Compound 237 | 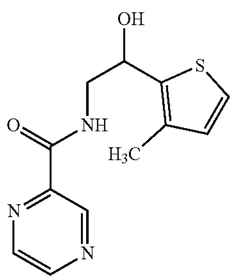 [SMILES: Cc1ccsc1C(O)CNC(=O)c1cnccn1] | F5857-1524 | | F5857-1524_1_1 (1 of 8) |
| Compound 238 | 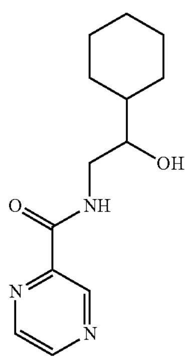 [SMILES: O=C(NCC(O)C1CCCCC1)c1cnccn1] | F5857-4935 | | F5857-4935_1_2 (1 of 8) |
| Compound 239 | 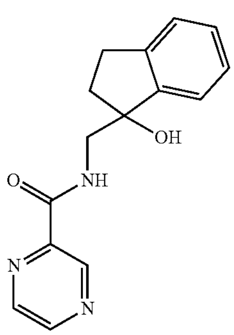 [SMILES: O=C(NCC1(O)CCc2ccccc21)c1cnccn1] | F5857-5314 | | F5857-5314_1_2 (1 of 8) |

TABLE 1-continued
| Compound x | Structure | No. | Tautomere/Stereoisomer | Reference of Variant |
|---|---|---|---|---|
| Compound 240 | 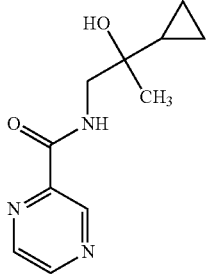 [SMILES: CC(O)(CNC(=O)c1cnccn1)C1CC1] | F5857-5693 | 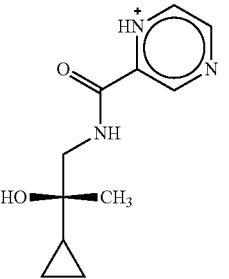 | F5857-5693_1_1 (1 of 8) |
| Compound 241 | 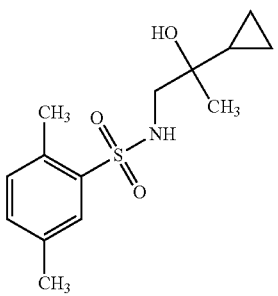 [SMILES: Cc1ccc(C)c(S(=O)(=O)NCC(C)(O)C2CC2)c1] | F5857-5862 | 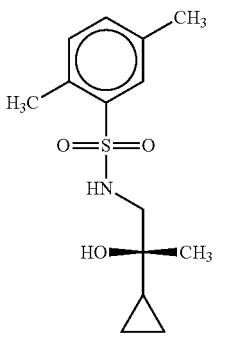 | F5857-5862_1 (1 of 2) |
| Compound 242 | 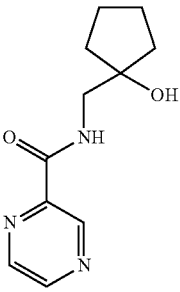 [SMILES: O=C(NCC1(O)CCCC1)c1cnccn1] | F5857-6072 | 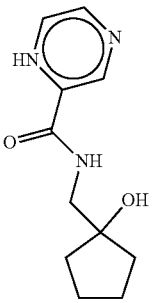 | F5857-6072_1_1 (1 of 4) |
| Compound 243 | 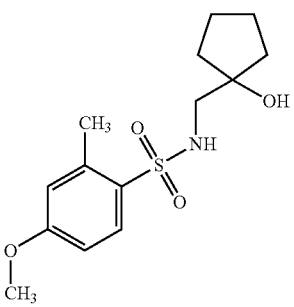 [SMILES: COc1ccc(S(=O)(=O)NCC2(O)CCCC2)c(C)c1] | F5857-6266 | 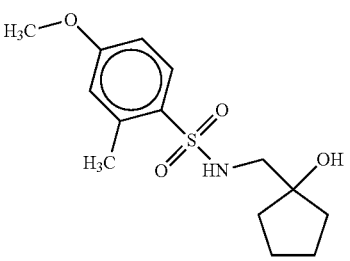 | F5857-6266_1 (1 of 1) |
| Compound 244 | 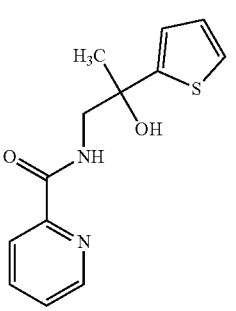 [SMILES: CC(O)(CNC(=O)c1ccccn1)c1cccs1] | F5857-7563 | 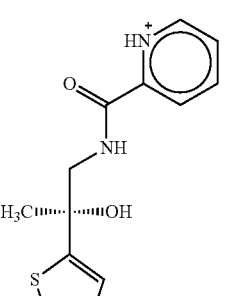 | F5857-7563_1_2 (1 of 4) |

TABLE 1-continued

| Compound x | Structure | No. | Tautomere/Stereoisomer | Reference of Variant |
|---|---|---|---|---|
| Compound 245 | 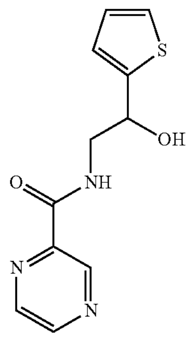 [SMILES: O=C(NCC(O)c1cccs1)c1cnccn1] | F5857-7901 | | F5857-7901_3_2 (1 of 8) |
| Compound 246 | 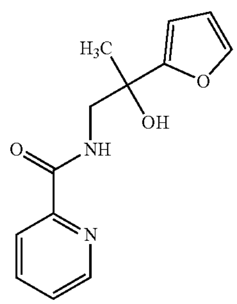 [SMILES: CC(O)(CNC(=O)c1ccccn1)c1ccco1] | F5857-9048 | | F5857-9048_1_2 (1 of 4) |
| Compound 247 | 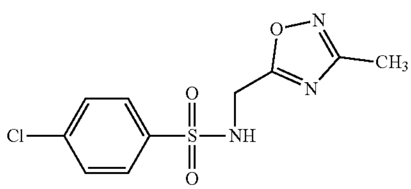 [SMILES: Cc1noc(CNS(=O)(=O)c2ccc(Cl)cc2)n1] | F5871-2878 | | F5871-2878_1 (1 of 2) |
| Compound 248 | 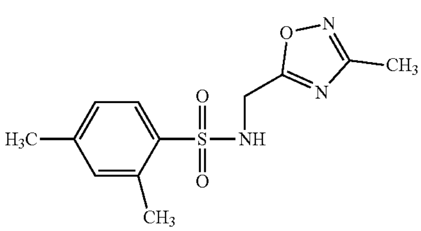 | F5871-2883 | | F5871-2883_1 (1 of 2) |

TABLE 1-continued

| Compound x | Structure | No. | Tautomere/Stereoisomer | Reference of Variant |
|---|---|---|---|---|
| Compound 249 | 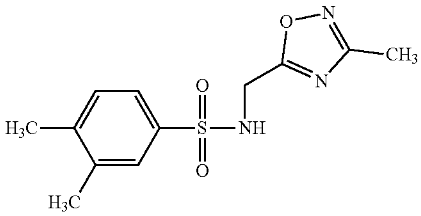 | F5871-2885 | | F5871-2885_1_1 (1 of 2) |
| Compound 250 | 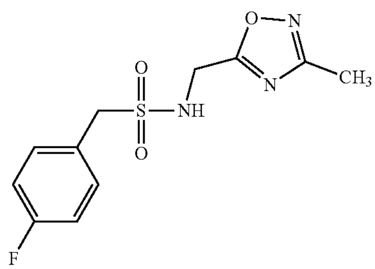 [SMILES: Cc1noc(CNS(=O)(=O)Cc2ccc(F)cc2)n1] | F5871-2898 | | F5871-2898_1 (1 of 2) |
| Compound 251 | 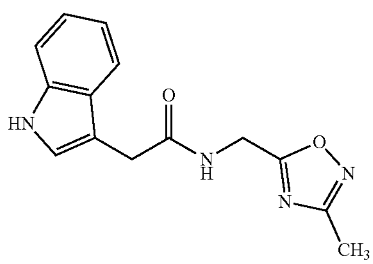 [SMILES: Cc1noc(CNC(=O)Cc2c[nH]c3ccccc23)n1] | F5871-3594 | | F5871-3594_1_1 (1 of 2) |
| Compound 252 | 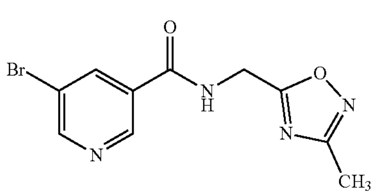 [SMILES: Cc1noc(CNC(=O)c2cncc(Br)c2)n1] | F5871-3603 | | F5871-3603_2_1 (1 of 3) |

TABLE 1-continued

| Compound x | Structure | No. | Tautomere/Stereoisomer | Reference of Variant |
|---|---|---|---|---|
| Compound 253 | 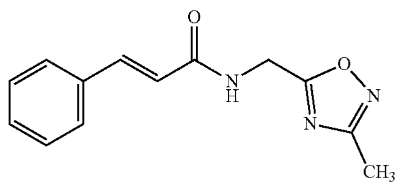 [SMILES: Cc1noc(CNC(=O)/C=C/c2ccccc2)n1] | F5871-3626 | | F5871-3626_1_1 (1 of 4) |
| Compound 254 | 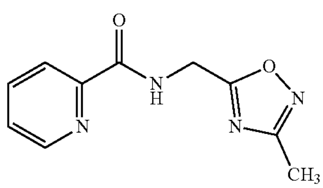 [SMILES: Cc1noc(CNC(=O)c2ccccn2)n1] | F5871-3665 | | F5871-3665_3_1 (1 of 4) |
| Compound 255 | 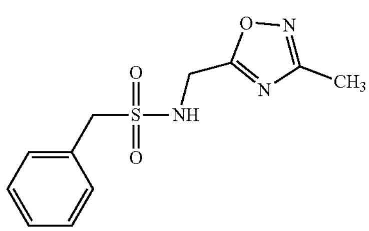 [SMILES: Cc1noc(CNS(=O)(=O)Cc2ccccc2)n1] | F5871-4854 | | F5871-4854_1 (1 of 2) |
| Compound 256 | 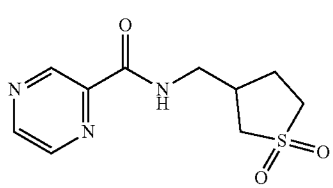 [SMILES: O=C(NCC1CCS(=O)(=O)C1)c1cnccn1] | F5882-4189 | | F5882-4189_1_1 (1 of 8) |

TABLE 1-continued

| Compound x | Structure | No. | Tautomere/Stereoisomer | Reference of Variant |
|---|---|---|---|---|
| Compound 257 | 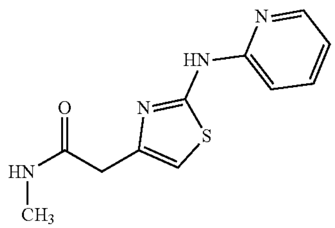 [SMILES: CNC(=O)Cc1csc(Nc2ccccn2)n1] | F5950-0041 | | F5950-0041_3_1 (1 of 4) |
| Compound 258 | 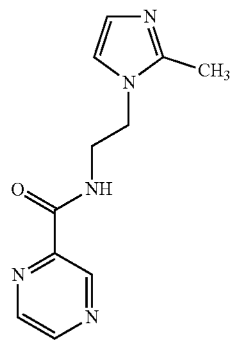 [SMILES: Cc1nccn1CCNC(=O)c1cnccn1] | F5959-0024 | | F5959-0024_1_1 (1 of 7) |
| Compound 259 | 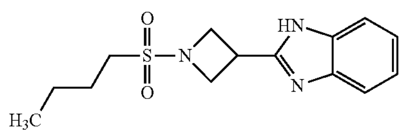 [SMILES: CCCCS(=O)(=O)N1CC(c2nc3ccccc3[nH]2)C1] | F6037-0307 | | F6037-0307_3_1 (1 of 4) |
| Compound 260 | 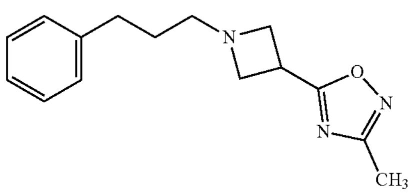 [SMILES: Cc1noc(C2CN(CCCc3ccccc3)C2)n1] | F6064-0318 | | F6064-0318_3_1 (1 of 4) |
| Compound 261 | 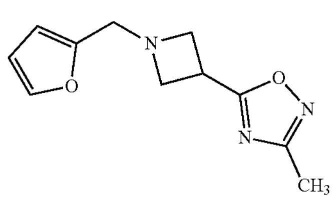 [SMILES: Cc1noc(C2CN(Cc3ccco3)C2)n1] | F6064-0331 | | F6064-0331_1_1 (1 of 4) |

TABLE 1-continued

| Compound x | Structure | No. | Tautomere/Stereoisomer | Reference of Variant |
|---|---|---|---|---|
| Compound 262 | 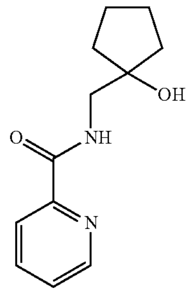 [SMILES: O=C(NCC1(O)CCCC1)c1ccccn1] | F6089-7863 | | F6089-7863_1_1 (1 of 2) |
| Compound 263 | 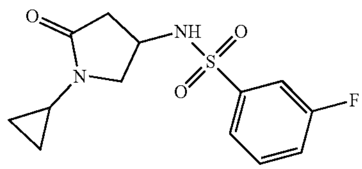 [SMILES: O=C1CC(NS(=O)(=O)c2cccc(F)c2)CN1C1CC1] | F6210-1183 | | F6210-1183_2 (1 of 2) |
| Compound 264 | 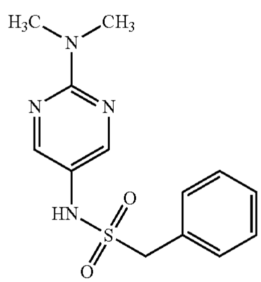 [SMILES: CN(C)c1ncc(NS(=O)(=O)Cc2ccccc2)cn1] | F6223-0039 | | F6223-0039_1_1 (1 of 2) |
| Compound 265 | 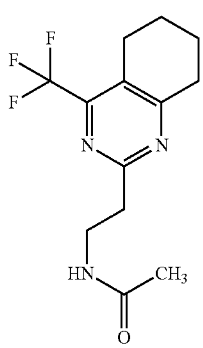 [SMILES: CC(=O)NCCc1nc2c(c(C(F)(F)F)n1)CCCC2] | F6286-0747 | | F6286-0747_1 (1 of 3) |

TABLE 1-continued

| Compound x | Structure | No. | Tautomere/Stereoisomer | Reference of Variant |
|---|---|---|---|---|
| Compound 266 | (structure) | F9995-0220 | (structure) | F9995-0220_22_1 (1 of 10) |
| Compound 267 | CH₃OC(O)CH₂C(O)CH₂C(O)CH₃ | F9999-0001 | | |
| Compound 268 | NH₂C(S)NH₂ | F9999-0002 | | |
| Compound 269 | (structure) | F9999-0003 | | |
| Compound 270 | (structure) | F9999-0004 | | |

Table 1 presents compounds of the present invention as well as examples of tautomers and stereoisomers, respectively, the number of potential tautomer or stereoisomers is indicated in brackets in column 5, "reference of variant".

A chemical modification of compounds 1 to 270 is any modification that results in a compound characterized by a specific and effective interaction with or binding to the dimerization site of MIA. Chemical modifications are for example selected from the group consisting of H, alkyl, cycloalkyl, heterocycloalkyl, alkenyl, alkynyl, aryl, heteroaryl or alkyl, arylalkyl, cycloalkylalkyl, heterocycloalkylalkyl, heteroaryalkyl, and alkoxyalkyl, each of which is optionally substituted one, two or three times with independently selected non-polar or polar groups.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)m, haloalkyl-S(O)m, alkenyl-S(O)m, alkynyl-S(O)m, cycloalkyl-S(O)m, cycloalkylalkyl-S(O)m, aryl-S(O)m, arylalkyl-S(O)m, heterocyclo-S(O)m, heterocycloalkyl-S(O)m, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxy acylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in lower alkenyl 1 to 4 carbon atoms) which include 1 to 4 double bonds in the normal chain.

Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)m, haloalkyl-S(O)m, alkenyl-S(O)m, alkynyl-S(O)m, cycloalkyl-S(O)m, cycloalkylalkyl-S(O)m, aryl-S(O)m, arylalkyl-S(O)m, heterocyclo-S(O)m, heterocycloalkyl-S(O)m, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system. having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, -0-. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —CI, —Br, and —I.

Compound 1 is represented by the following general Formula (I)

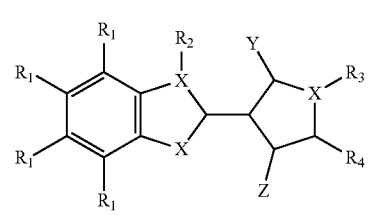

Formula (I)

wherein, $R_1$, $R_2$ and $R_4$ represent, independent of each other, hydrogen, halogens, alkyls, alkenyls, alkynyls, cycloalkyls or aryls;

$R_3$ represents a linear $n_{1-7}$ alkyl, a branched $n_{3-7}$ alkyl, a linear $n_{1-7}$ alkenyl, a branched $n_{3-7}$ alkenyl, a linear $n_{1-7}$ alkynyl, a branched $n_{3-7}$ alkynyl, a $n_{5-7}$ cycloalkyl, a $n_{5-7}$ cycloalkenyl, a $n_{5-7}$ cycloalkynyl, a $n_{5-7}$ aryl;

X represents, independent of each other, a substituted or unsubstituted heteroatom selected from N and S, wherein the heteroatom may form a double bond with a neighboring carbon atom;

Y represents a substituted or unsubstituted amine which may form a double bond with a neighboring carbon atom; and Z represents a halogen or a substituted or unsubstituted heteroatom selected from O, N and S, wherein the heteroatom may form a double bond with a neighboring carbon atom.

Compound 1 comprises for example the following modifications:

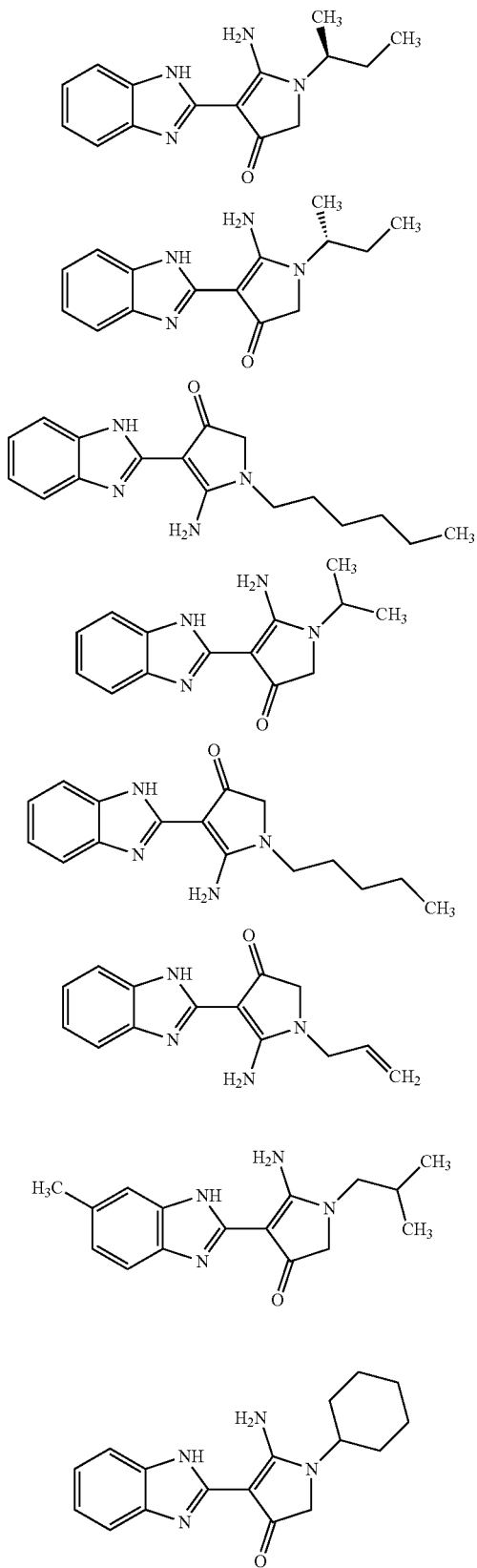

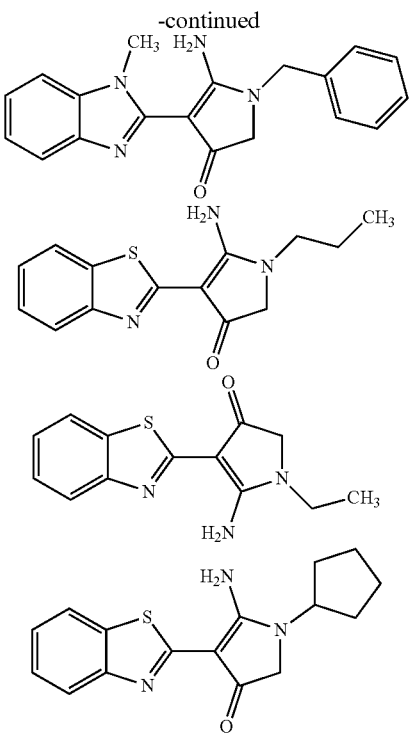

Compound 2 is represented by the following general Formula (II)

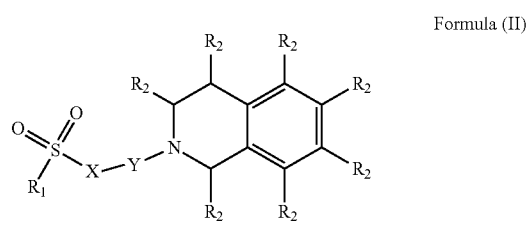

wherein, $R_1$ represents a hydrogen, alkyl, alkenyl, alkynyl, amin, aminoalkyl, aminoalkenyl, halogens, alkyls, alkenyls, alkynyls, cycloalkyls or aryl;

$R_2$ represents, independent from each other, a hydrogen, alkyl, alkenyl, or alkynyl;

X represents a substituted or unsubstituted heteroatom selected from N and S; and Y represents a linear $n_{3-5}$ alkyl, a linear $n_{3-5}$ alkenyl, or a linear $n_{3-5}$ alkynyl.

Compound 2 comprises for example the following modifications:

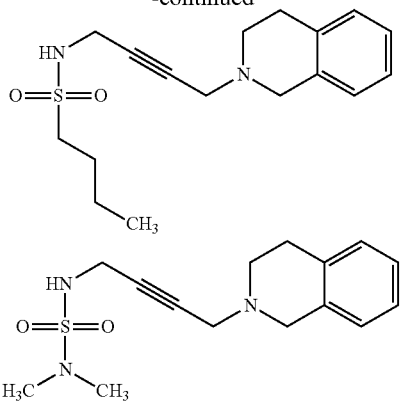

Compound 3 is represented by the following general Formula (III) wherein,

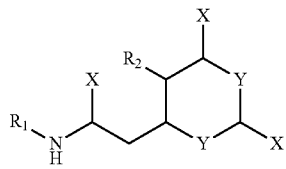

Formula (III)

$R_1$ represents a hydrogen, linear $n_{3-5}$ alkyl, a linear $n_{3-5}$ alkenyl, a linear $n_{3-5}$ alkynyl, a linear $n_{3-5}$ hydroxlylalkyl, a linear $n_{3-5}$ hydroxlylalkenyl, a linear $n_{3-5}$ hydroxlylalkynyl, a linear $n_{3-5}$ ethoxylylalkyl, a linear $n_{3-5}$ ethoxylylalkenyl, or a linear $n_{3-5}$ ethoxylylalkynyl;

$R_2$ represents a hydrogen, halogen, alkyl, alkenyl, or alkynyl;

X represents a hydroxyl or a =O group;

Y represents, independent of each other, a heteroatom selected from N and S, wherein the heteroatom may form a double bond with a neighboring carbon atom.

Compound 3 comprises for example the following modifications:

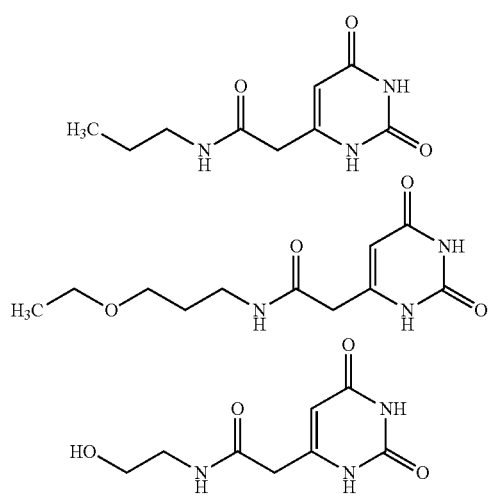

Compound 4 is represented by the following general Formula (IV)

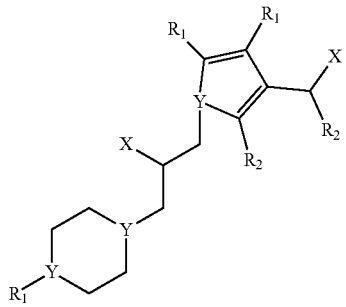

Formula (IV)

wherein, $R_1$ represents, independent from each other, a hydrogen, halogen, alkyl, alkenyl, or alkynyl;

$R_2$ represents, independent from each other, a hydrogen, halogen, alkyl, alkenyl, alkynyl or wherein the $R_2$ residues together form a $n_{5-7}$ cycloalkyl or an $n_{5-7}$ aryl;

X represents a hydrogen, a hydroxyl or a =O group;

Y represents, independent from each other, a carbon atom or a heteroatom selected from N and S, wherein the heteroatom may form a double bond with a neighboring carbon atom.

Compound 4 comprises for example the following modifications:

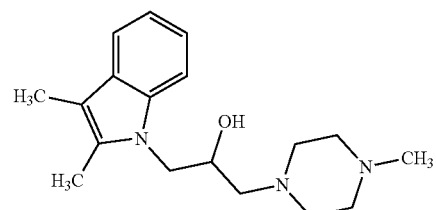

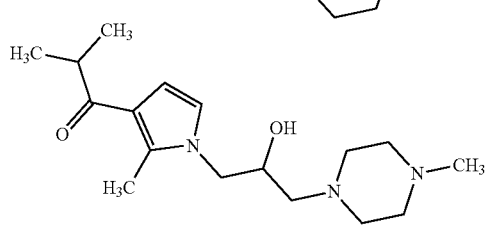

Compound 5 is represented by the following general Formula (V)

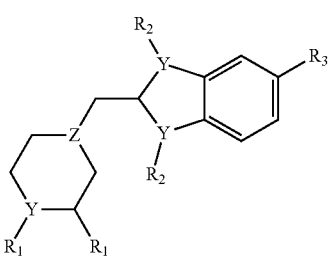

Formula (V)

wherein,

R₁ represents, independent of each other, a hydrogen, alkyl, alkenyl, or alkynyl, or wherein two R₁ form a cycloalkyl or an aryl;

R₂ represents, independent of each other, a hydrogen, alkyl, alkenyl, or alkynyl;

R₃ represents a hydrogen, halogen, ethoxyl, alkyl, alkenyl, or alkynyl;

Y represents, independent of each other, a heteroatom selected from N and S, wherein the heteroatom may form a double bond with a neighboring carbon atom; and Z represents a carbon atom or N.

Compound 5 comprises for example the following modifications:

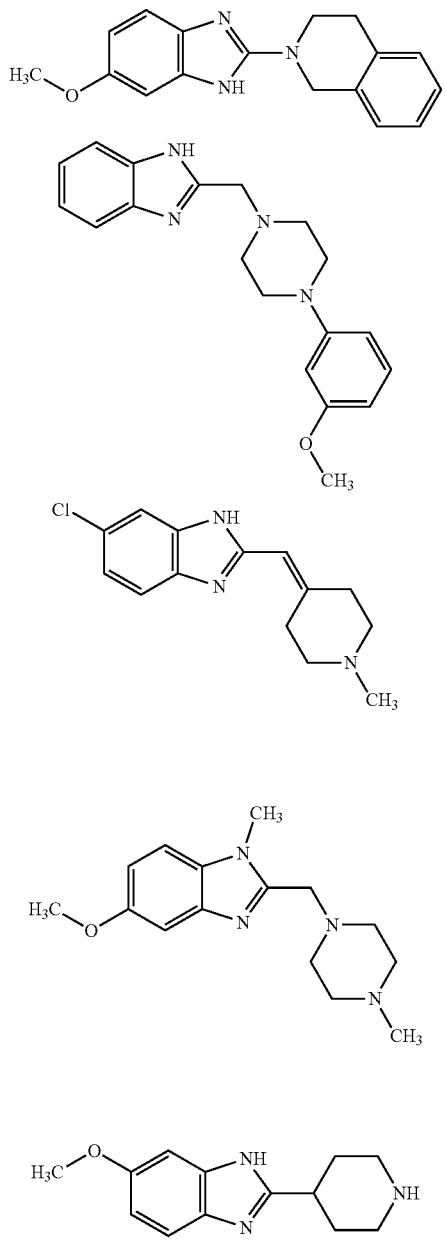

Compound 6 is represented by the following general Formula (VI)

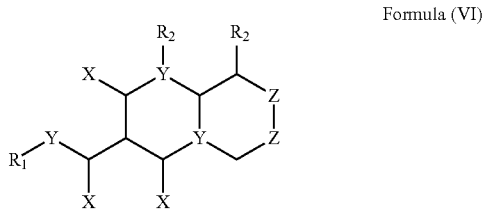

Formula (VI)

wherein,

R₁ represents a linear $n_{2-6}$ alkyl, a branched $n_{3-6}$ alkyl, a linear $n_{2-6}$ alkenyl, a branched $n_{3-6}$ alkenyl, a linear $n_{2-6}$ alkynyl, a branched $n_{3-6}$ alkynyl, a $n_{5-7}$ cycloalkyl, a $n_{5-7}$ cycloalkenyl, a $n_{5-7}$ cycloalkynyl, a $n_{5-7}$ arylalkyl, a $n_{1-3}$ alkylcarboxyl;

R₂ represents, independent of each other, a hydrogen, alkyl, alkenyl, or alkynyl;

Y represents, independent of each other, a heteroatom selected from N and S, wherein the heteroatom may form a double bond with a neighboring carbon atom; and Z represents, independent of each other, a carbon atom which may form a double bond with a neighboring carbon atom.

Compound 6 comprises for example the following modifications:

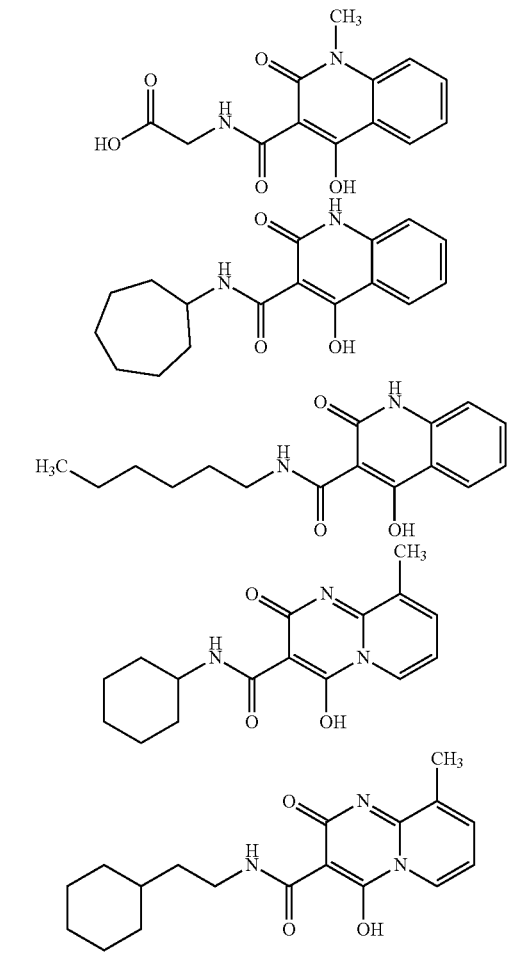

-continued

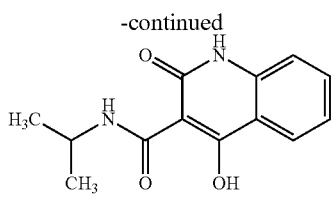

The present invention is not only directed to the non-hydrophobic compounds of Table 1, to the tautomers and stereoisomers thereof, but also to chemically modified forms of these compounds as mentioned for example above.

The metastasis preventable and/or treatable by use of a compound of the present invention is based on any type of primary tumor for example melanoma, breast cancer, glioma, pancreas carcinoma, and colon carcinoma. In one embodiment, the primary tumor is a late stage tumor. The metastasis is for example located in the liver, lung, bone, colon, stomach, nerves, lymph nodes, skin and/or brain.

The cartilage defect preventable and/or treatable by use of a compound of the present invention is for example a degenerative disorder of cartilage selected from rheumatoid arthritis, degeneration of cartilage in a joint, degenerative disc disease, meniscus tears, anterior crucial ligament (ACL) injury, arthritis, osteoarthritis, psoriatic arthritis, juvenile chronic arthritis, rhizomelic arthritis, rheumatoid poly-arthritis, synovitis and villonodular synovitis.

The dimerization of the MIA protein is for example measured by a heterogeneous transition metal-based fluorescence polarization (HTFP) assay, wherein the ratio $P/P_0$ is measured. P is the fluorescence polarization signal of a MIA protein labeled with a transition metal complex in the presence of substrate bound MIA-protein and of a compound to be tested. $P_0$ is the fluorescence polarization signal of free MIA-protein labeled with said luminescent transition metal complex in the absence of substrate bound MIA-protein and in the absence of the compound. In the absence of the compound, usually, the labeled MIA-protein would interact with the substrate bound MIA-protein, which, in turn, would contribute to a reduction in rotational mobility of the labeled MIA-protein, and therefore, the fluorescence polarization signal would increase upon such interaction. If, additionally, a compound is present that interferes with such interaction, no or little dimerization/aggregation occurs and no or little increase in fluorescence polarization signal would be detected. The smaller or even more negative $P/P_0$ is, the stronger such interference with dimer formation and aggregation is, and the better such compound prevents or breaks up dimerization/aggregation of MIA protein. In an alternative embodiment, binding of the compound to MIA protein is determined by NMR, e.g., heteronuclear NMR, e.g., $^{15}$N-$^1$H-HSQC-NMR.

In the present invention at least one compound of 1 to 270 of Table 1, a tautomer, a stereoisomer or a chemically modified compound thereof is administered to a subject, or in another embodiment two or more of these compounds, tautomers, stereoisomers and/or chemically modified compounds thereof are administered to a subject for use in preventing and/or treating of metastasis or a cartilage defect. The compounds are administered at the same time or consecutively.

In one embodiment the size of compounds of the present invention is increased by compound growing or compound linking. Regarding fragment growing an initial compound is steadily build up to explore favorable interactions with adjacent regions of the dimerization site; and regarding compound linking compounds of the present invention (e.g., two or more for example 3, 4, 5, 6, 7, 8, 9, 10) are connected to each other, i.e., are coupled with or without a linker.

In an embodiment of the present invention the compounds are hydrophobic, in another embodiment the compounds are hydrophilic or neutral.

In another embodiment one or more compounds of the present invention are administered to a subject in combination with a chemotherapeutic which is any chemical agent, e.g., naturally occurring or synthesized, effective in the treatment of cancer such as Vermurafenib, Ipilimumab, Trametinib, Dabradenib, Dacarbazine, Paclitaxel, Carboplatin, Interferon-alpha and Aldesleukin, TGF alpha, TGF beta, interleukin etc. The compound and the chemotherapeutic are administered at the same time or consecutively.

The present invention further refers to a pharmaceutical composition for use in preventing and/or treating of metastasis caused by the dimerization of melanoma inhibitory activity (MIA) protein and/or a cartilage defect, wherein regeneration is inhibited by MIA dimerization, wherein the pharmaceutical composition comprises at least one compound selected from the group consisting of compound 1 to 270 of Table 1, tautomers, stereoisomers and/or chemically modified compounds thereof, and a pharmaceutically acceptable carrier and/or solvent. The pharmaceutical composition may further comprise a chemotherapeutic or any substance, including cells such as chondrocytes, positively influencing cartilage growth and regeneration, respectively.

EXAMPLES

The following examples show the present invention in more detail, however, the invention is not limited to these examples.

Example 1

Fragment-based in silico screening was applied to identify the small, fragment-sized compounds of the present invention that inhibit MIA. The suggested structures were screened in vitro and modular synthesis strategies were developed for the most promising molecules.

NMR Titration Experiment

Derived from HSQC titrations of $^{15}$N-labeled MIA with AR71 (a peptide having the amino acid sequence FHWRY-PLPLPGQ (SEQ ID NO:1)), the amino acids CYS17, SER18, TYR47, GLY66, ASP67, LEU76, TRP102, ASP103, and CYS106 were found to exhibit strong shift perturbations (Schmidt, J., A. Riechers, and A. K. Bosserhoff, *MIA—a new target protein for malignant melanoma therapy*. Histol Histopathol, 2013. 28(4): p. 421-6) and were defined as interacting residues in an in silico protein-peptide docking of MIA and AR71. The resulting model shows the binding of the peptide in the hydrophobic cleft, which forms part of the dimerization domain.

Virtual Screening

The 1.4 Å resolution crystal structure of human MIA protein 1I1J (Lougheed, J. C., et al., *Structure of melanoma inhibitory activity protein, a member of a recently identified family of secreted proteins*. Proceedings of the National Academy of Sciences, 2001, 98(10): p. 5515-5520) and the first model of each of the NMR solution structures 1K0X (Lougheed, J., P. Domaille, and T. Handel, *Solution structure and dynamics of melanoma inhibitory activity protein*. Journal of Biomolecular NMR, 2002, 22(3): p. 211-223) and 1HJD (Stoll, R., et al., *The extracellular human melanoma inhibitory activity (MIA) protein adopts an SH3 domain-like* fold. 2001. 20(3): p. 340-349) were used as distinct MIA protein receptor conformations for the virtual screening experiment. The same amino acid residues that were used in the protein-peptide docking were provided as input to the molecular docking software in order to guide the automated detection and definition of putative binding sites in the MIA protein.

In each of the three MIA protein conformations the same single putative binding site was detected. The site is located in a cleft near the distal loop (residues 69 to 75) and is framed by the solvent exposed "disulfide loop" (residues 13 to 19), the turn of the RT loop (residues 35-38), and the C-terminal residues 102 to 106. Most of the amino acid residues identified to interact with the AR71 peptide by induced chemical shift changes constitute to the putative binding site, with the exception of TYR48, GLY66, and ASP67, which are located on the distal loop and thus too far away. Differences in the arrangement of the structural elements surrounding the cleft within each of the three distinct MIA receptor conformations result in a different volume and shape of the putative binding site.

Fragment library preparation commenced with 28751 fragment structures that were contained within the unprocessed fragment library catalogue obtained from the compound provider. Filtering for salts, unwanted chemistry and functional groups, as well as duplicate structures led to the removal of 1, 2577 and 127 structures, respectively. Each of the remaining 26046 structures was subjected to complete enumeration of its protonation and tautomeric states, which led to 87270 protomer variants for all fragment structures. Subsequently, all stereoisomers were enumerated for the protomer variants, which resulted in 124590 fragment variants. Generation of 3D conformations allowed for up to five alternate ring conformations per fragment variant and produced a final library of 217176 fragment variant conformations, which were docked into the three MIA receptor conformations with their respective putative binding sites.

The resulting docking poses were subjected to a filtering and ranking workflow, which, for each MIA protein conformation, determined a list of fragments ranked by the empirical scoring function of the docking software. The ten highest-ranking fragments for each MIA receptor conformation were selected for experimental testing.

All listed compounds that were screened for their ability to interfere with the MIA-MIA interaction (Table 1) in a heterogeneous transition metal-based fluorescence polarization (HTFP) assay previously developed (Riechers, A., et al., *Heterogeneous transition metal-based fluorescence polarization (HTFP) assay for probing protein interactions*. Biotechniques, 2009. 47(4): p. 837-44). This screening revealed significant decreases in the fluorescence polarization of Ru-(bpy)$_3$, labelled MIA for compounds 1, 2, 3, 4, 5, and 6; the results are shown in FIG. 3. The molecular structures of the compounds showing interference with the MIA-MIA interaction in the HTFP assay are shown in Table 1.

Example 2

Boyden chamber migration assays (Stoll, R., Lodermeyer, S. & Bosserhoff, A. K. Detailed analysis of MIA protein by mutagenesis. Biol Chem 387, 1601-1606, (2006)) using human Mel-Im melanoma cells demonstrated a reduction in the MIA activity on melanoma cell migration in the presence of compounds 1, 2, 3, 4, 5, and 6 at a concentration of 1 µM as shown in FIG. 4.

The melanoma cell line Mel-Im, established from a human metastatic bioptic sample (generous gift from Dr. Johnson, University of Munich, Germany) was used for the Boyden chamber migration experiments. All cells were maintained in DMEM (PAA, Pasching, Germany) supplemented with penicillin (400 U/mL), streptomycin (50 µg/mL), L-glutamine (300 µg/mL) and 10% fetal calf serum (Pan Biotech GmbH, Aidenbach, Germany) and split in a 1:6 ratio every three days. Migration assays were performed in Boyden Chambers containing polycarbonate filters with 8-nm pore size (Neuro Probe, Gaithersburg, Md., USA) essentially as described. MIA was added to the cell suspension at a final concentration of 200 ng/mL. Selected compounds were used at a final concentration of 1 µM. Experiments were carried out in triplicates and repeated at least three times.

Example 3

In order to assess whether compounds of the present invention show any adverse effects on normal cells, human fibroblasts and kidney cells were treated with the compounds 1, 2, 3, 4, 5, and 6, respectively, in vitro at a concentration of 7.8 µM in analogy to previous studies (Schmidt, J., et al., *Targeting melanoma metastasis and immunosuppression with a new mode of melanoma inhibitory activity (MIA) protein inhibition*. PLoS One, 2012. 7(5): p. e37941; Riechers, A., et al., *Heterogeneous transition metal-based fluorescence polarization (HTFP) assay for probing protein interactions*. Biotechniques, 2009. 47(4): p. 837-44). There were no negative effects on the proliferation of human fibroblasts (FIG. 5A) and kidney cells (FIG. 5C) as well as cellular attachment of the same cell types (FIGS. 5B and 5D) in the presence of the compounds.

A significant decrease in proliferation of the human melanoma cell line Mel Im after treatment with compound 1 was observed as presented in (FIG. 6). A phenomenon that could not be found with the other compounds 2, 3, 4, 5 or 6.

The invention claimed is:

1. A method of preventing the occurrence of and/or treating a subject for metastasis caused by the dimerization of melanoma inhibitory activity (MIA) protein or of a cartilage defect, wherein regeneration is inhibited by MIA dimerization, the method comprising:
 administering to the subject a composition comprising a compound that is non-hydrophobic, wherein the compound is selected from the group consisting of
 5-amino-4-(1H-1,3-benzodiazol-2-yl)-1-(butan-2-yl)-2,3-dihydro-1H-pyrrol-3-one,
 N-[4-(1,2,3,4-tetrahydroisoquinolin-2-yl)but-2-yn-1-yl]methanesulfonamide,
 2-(2,6-dioxo-1,2,3,6-tetrahydropyrimidin-4-yl)-N-pentylacetamide,
 1-{1-[2-hydroxy-3-(piperazin-1-yl)propyl]-2,4-dimethyl-1H-pyrrol-3-yl}ethan-1-one,
 5-methoxy-2-(piperazin-1-ylmethyl)-1H-1,3-benzodiazole, and
 N-butyl-2-hydroxy-9-methyl-4-oxo-4H-pyrido[1,2-a]pyrimidine-3-carboxamide.

2. The method according to claim 1, wherein the compound is
 5-methoxy-2-(piperazin-1-ylmethyl)-1H-1,3-benzodiazole.

3. The method according to claim 1, wherein the metastasis is based on a primary tumor that is an MIA-expressing tumor.

4. The method according to claim 3, wherein the primary tumor is selected from the group consisting of melanoma, breast cancer, glioma, pancreas carcinoma, and colon carcinoma.

5. The method according to claim 1, wherein the metastasis is located in the liver, lung, bone, colon, stomach, nerves, lymph nodes, skin and/or brain.

6. The method according to claim 1, wherein the composition is administered orally.

7. The method according to claim 1, further comprising:
 administering a chemotherapeutic to the subject.

8. The method according to claim 7, wherein the chemotherapeutic is selected from the group consisting of Vemurafenib, Ipilimumab, Trametinib, Dabradenib, Dacarbazine, Paclitaxel, Carboplatin, Interferon-alpha and Aldesleukin.

9. The method according to claim 7, wherein the composition and the chemotherapeutic are administered at the same time.

10. A method for preventing the occurrence of and/or treating a subject for a metastasis caused by the dimerization of melanoma inhibitory activity (MIA) protein and/or a cartilage defect, wherein regeneration is inhibited by MIA dimerization, the method comprising:
 administering to the subject a pharmaceutical composition comprising:
  at least one compound selected from the group consisting of 5-amino-4-(1H-1,3-benzodiazol-2-yl)-1-(butan-2-yl)-2,3-dihydro-1H-pyrrol-3-one,
 N-[4-(1,2,3,4-tetrahydroisoquinolin-2-yl)but-2-yn-1-yl]methanesulfonamide,
 2-(2,6-dioxo-1,2,3,6-tetrahydropyrimidin-4-yl)-N-pentylacetamide,
 1-{1-[2-hydroxy-3-(piperazin-1-yl)propyl]-2,4-dimethyl-1H-pyrrol-3-yl}ethan-1-one,
 5-methoxy-2-(piperazin-1-ylmethyl)-1H-1,3-benzodiazole, and
 N-butyl-2-hydroxy-9-methyl-4-oxo-4H-pyrido[1,2-a]pyrimidine-3-carboxamide, and
 a pharmaceutically acceptable carrier and/or solvent.

11. The method according to claim 10, further comprising:
 administering a chemotherapeutic to the subject.

12. The method according to claim 10, wherein the compound is
 5-methoxy-2-(piperazin-1-ylmethyl)-1H-1,3-benzodiazole.

13. The method according to claim 7, wherein the chemotherapeutic is selected from the group consisting of vermurafenib, ipilimumab, trametinib, dabradenib, dacarbazine, paclitaxel, carboplatin, interferon-α, and aldesleukin.

14. The method according to claim 10, wherein the pharmaceutical composition further comprises a chemotherapeutic.

15. The method according to claim 7, wherein the composition and the chemotherapeutic are administered consecutively.

16. The method according to claim 8, wherein the composition and the chemotherapeutic are administered at the same time.

17. The method according to claim 8, wherein the composition and the chemotherapeutic are administered consecutively.

18. A method of treating a subject in need thereof by inhibiting melanoma inhibitory activity protein (MIA)—MIA dimerization, the method comprising:
 administering to the subject a composition comprising a non-hydrophobic compound selected from the group consisting of
 5-amino-4-(1H-1,3-benzodiazol-2-yl)-1-(butan-2-yl)-2,3-dihydro-1H-pyrrol-3-one,
 N-[4-(1,2,3,4-tetrahydroisoquinolin-2-yl)but-2-yn-1-yl]methanesulfonamide,
 2-(2,6-dioxo-1,2,3,6-tetrahydropyrimidin-4-yl)-N-pentylacetamide,
 1-{1-[2-hydroxy-3-(piperazin-1-yl)propyl]-2,4-dimethyl-1H-pyrrol-3-yl}ethan-1-one,
 5-methoxy-2-(piperazin-1-ylmethyl)-1H-1,3-benzodiazole, and
 N-butyl-2-hydroxy-9-methyl-4-oxo-4H-pyrido[1,2-a]pyrimidine-3-carboxamide.

19. The method according to claim 18, wherein the subject has a primary tumor.

20. The method according to claim 18, wherein the compound is administered orally.

21. The method according to claim 18, wherein the compound is
 5-methoxy-2-(piperazin-1-ylmethyl)-1H-1,3-benzodiazole.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Peptide

<400> SEQUENCE: 1

Phe His Trp Arg Tyr Pro Leu Pro Leu Pro Gly Gln
1               5                   10